United States Patent [19]
Gunther et al.

[11] Patent Number: 5,923,571
[45] Date of Patent: Jul. 13, 1999

[54] APPARATUS AND METHOD FOR AUTOMATIC CONGRUENT CONTROL OF MULTIPLE BOILERS SHARING A COMMON FEEDWATER LINE AND CHEMICAL FEED POINT

[75] Inventors: John C. Gunther, Bensalem; Haiwen Chen, Holland; John A. Muccitelli, Oreland, all of Pa.

[73] Assignee: BetzDearborn, Inc., Trevose, Pa.

[21] Appl. No.: 08/944,921

[22] Filed: Oct. 6, 1997

Related U.S. Application Data

[63] Continuation-in-part of application No. 08/321,338, Oct. 11, 1994, Pat. No. 5,696,696.

[51] Int. Cl.$^6$ .................................................. G01N 27/00
[52] U.S. Cl. ............................... 364/528.02; 364/528.01; 364/528.17; 702/31; 702/22; 702/30
[58] Field of Search ................................. 702/22, 23, 27, 702/30–32, 45, 50, 55, 176, 177, 183; 364/528.01, 528.02, 528.09, 528.17, 528.2, 528.41, 151, 152, 148.01–148.09, 148.1, 149, 150, 153, 164–166, 578, 157, 132, 159; 422/62, 12, 14, 16, 110, 111, 81; 436/55, 56, 50; 376/216, 217; 237/8 A; 210/743, 742, 739, 96.1, 103, 311–313, 85–89; 706/906, 907, 914, 915

[56] References Cited

U.S. PATENT DOCUMENTS

| | | | |
|---|---|---|---|
| 2,842,311 | 7/1958 | Petrie | 364/150 |
| 3,011,709 | 12/1961 | Jacoby | 364/150 |
| 3,462,364 | 8/1969 | Carlson | 210/709 |
| 3,792,244 | 2/1974 | Wilke | 364/528.02 |
| 3,804,253 | 4/1974 | Wellman et al. | 210/85 |
| 3,891,836 | 6/1975 | Lee | 364/132 |
| 4,016,079 | 4/1977 | Severin | 210/96.1 |
| 4,033,871 | 7/1977 | Wall | 210/96.1 |

(List continued on next page.)

FOREIGN PATENT DOCUMENTS 0640 747 A1  3/1995  European Pat. Off. .

OTHER PUBLICATIONS

Brestel, L. O., Power, Oct. 1987, 61–65.
Rogers, et al., Corrosion 92, 1992, Paper No. 413 (No date with month), (1–10).
Economy, et al., Sodium Phosphate Solutions at Boiler Conditions: Solubility, Phase Equilibria, and Interations with Magnetite, Jul. 12, 1994, 162–173.
Abstract, A Practical Approach To Real Time Data Acquisition and Automated Chemical Feed at a Fossil Fueled Cycling Duty Station, (No date with month).

*Primary Examiner*—Hal Dodge Wachsman
*Attorney, Agent, or Firm*—Caesar, Rivise, Bernstein Cohen & Pokotilow, Ltd.

[57] ABSTRACT

Two control methods and systems for automatically achieving and maintaining a desired sodium/phosphate ratio and phosphate concentration of the boiler waters in a plurality of parallel industrial boilers linked by a common feedwater line for minimizing corrosion. The first control system uses an adaptive controller that models the boilers which enables the system to predict boiler pH and phosphate concentrations at any future time given the feed rates, feed concentrations of high and low sodium/phosphate stocks, blowdown rate, mass of the boiler water, initial boiler phosphate concentration and initial pH. Once these future concentrations are determined, the controller then determines a common normalized control (target) region among all the boilers and feed rates that will drive at least one of the boilers into that region in the least amount of time. Subsequent iterations of feed rates are made based on updated boiler water concentrations to drive all of the boiler waters into that target region. The second control system monitors a maximum cycle boiler ratio to keep the boiler waters within the phosphate control range of the system. This arrangement allows for the control of sodium by switching between the high and low ratio sodium/phosphate stocks based on the average sodium-to-phosphate ratio among all the boilers with respect to a desired average predetermined sodium-to-phosphate ratio.

68 Claims, 8 Drawing Sheets

5,923,571
Page 2

U.S. PATENT DOCUMENTS

| | | | |
|---|---|---|---|
| 4,053,743 | 10/1977 | Niemi | 364/528.02 |
| 4,181,951 | 1/1980 | Boeke | 364/528.02 |
| 4,236,220 | 11/1980 | Kogami et al. | 376/217 |
| 4,239,493 | 12/1980 | Niemi et al. | 436/55 |
| 4,349,869 | 9/1982 | Prett et al. | 364/159 |
| 4,406,794 | 9/1983 | Brigante | 210/96.1 |
| 4,644,479 | 2/1987 | Kemper et al. | 702/185 |
| 4,659,459 | 4/1987 | O'Leary et al. | 210/87 |
| 4,736,316 | 4/1988 | Wallman | 364/149 |
| 4,770,843 | 9/1988 | Taleyarkhan | 376/216 |
| 4,833,622 | 5/1989 | Barto et al. | 364/528.06 |
| 4,897,797 | 1/1990 | Free, Jr. et al. | 364/528.01 |
| 5,038,270 | 8/1991 | Tozawa et al. | 364/148.01 |
| 5,040,725 | 8/1991 | Butler | 237/8 R |
| 5,041,386 | 8/1991 | Pierce et al. | 436/50 |
| 5,057,229 | 10/1991 | Schulenburg | 210/743 |
| 5,083,281 | 1/1992 | Rabindran et al. | 364/478.08 |
| 5,132,916 | 7/1992 | Gulaian et al. | 364/528.02 |
| 5,141,716 | 8/1992 | Muccitelli et al. | 422/16 |
| 5,152,252 | 10/1992 | Bolton et al. | 122/401 |
| 5,164,159 | 11/1992 | Hayashi et al. | 422/81 |
| 5,218,526 | 6/1993 | Mozzo | 364/152 |
| 5,248,577 | 9/1993 | Jerome | 430/30 |
| 5,262,963 | 11/1993 | Stana et al. | 364/528.01 |
| 5,288,713 | 2/1994 | Reese | 210/696 |
| 5,320,967 | 6/1994 | Avallone et al. | 436/50 |
| 5,347,446 | 9/1994 | Iino et al. | 364/149 |
| 5,422,014 | 6/1995 | Allen et al. | 364/528.02 |
| 5,424,942 | 6/1995 | Dong et al. | 364/164 |
| 5,455,763 | 10/1995 | Feingold | 364/149 |
| 5,486,995 | 1/1996 | Krist et al. | 364/149 |
| 5,516,423 | 5/1996 | Conoby et al. | 210/85 |
| 5,519,605 | 5/1996 | Cawlfield | 364/151 |
| 5,521,814 | 5/1996 | Teran et al. | 364/528.01 |
| 5,568,377 | 10/1996 | Seem et al. | 364/157 |
| 5,587,897 | 12/1996 | Iida | 364/148.01 |

APPARATUS AND METHOD FOR AUTOMATIC CONGRUENT CONTROL OF MULTIPLE BOILERS SHARING A COMMON FEEDWATER LINE AND CHEMICAL FEED POINT

RELATED APPLICATIONS

This application is a Continuation-in-Part of application Ser. No. 08/321,338 filed Oct. 11, 1994, now U.S. Pat. No. 5,696,696, entitled APPARATUS AND METHOD FOR AUTOMATICALLY ACHIEVING AND MAINTAINING CONGRUENT CONTROL IN AN INDUSTRIAL BOILER, assigned to the same Assignee as the present invention and whose disclosure is incorporated by reference herein.

SPECIFICATION

FIELD OF THE INVENTION

The invention pertains to automatic control systems for continuously stirred tank reactors (CSTRs). In particular, the invention pertains to automatic control systems for realizing optimum congruency and phosphate concentration required to minimize corrosion in industrial high pressure boilers.

BACKGROUND OF INVENTION

Industrial boilers heat up highly purified feedwater to generate steam for power generation, heating, etc.

A natural consequence of steam production is the "cycling up" in concentration of chemicals which enter the boiler inadvertently (e.g., acid leaks) or intentionally (e.g., corrosion inhibitors). A small portion of the boiler water is "blown down" (i.e., removal of concentrated boiler water from the boiler) to keep the concentrations of non-volatile chemicals (i.e., chemicals that do not flow out with the steam but rather remain substantially in the boiler water) at acceptable levels. The rate of blowdown is defined by the "cycles of concentration." The term "cycles of concentration" is defined as the sum of the steam and blowdown flowrates divided by the blowdown flowrate. Cycles in high pressure boilers range from less than 10 to 100 or more. Thus a chemical added at a low concentration (e.g., 0.5 ppm) in the feedwater can cycle up to fairly high boiler concentrations (e.g., 30 ppm).

These boilers are susceptible to, among other things, corrosion. To minimize corrosion, one basic type of corrosion control program that is practiced in the United States within these boilers is phosphate control programs. Typically, in phosphate control programs, a sodium phosphate salt is fed into the solution in order to buffer the solution and to maintain that pH with sodium. The objective of these phosphate control programs is to maintain the measured variables, phosphate and pH, within certain stated guidelines, which are dependent upon boiler pressure by controlling the sodium, phosphate and resultant pH within the boiler water. See "Sodium Phosphate Solutions at Boiler Conditions: Solubility, Phase Equilibria, and Interactions with Magnetite," by G. Economy, A. J. Panson, Chia-tsun Liu, J. N. Esposito, and W. T. Lindsay, Jr., *Proc. Intl. Water Conf.* 1975, pp. 161–173.

If the concentration of sodium within the boiler water (which is given by the pH, i.e., pH is proportional to effective sodium) is divided by the concentration of phosphate within the boiler water, there exists a range of optimum sodium-to-phosphate ($Na/PO_4$) ratios that, if achieved and maintained within the boiler water, will minimize corrosion. Where the boiler water is operated and maintained at a $Na/PO_4$ ratio that is below 3.0:1, the boiler is said to be operating with coordinated phosphate/pH control (also known as "captive alkalinity"). Where the boiler water is operated and maintained at a $Na/PO_4$ ratio that is between 2.2:1 and 2.8:1, the boiler is said to be operating with congruent control. Where the boiler is water is operated at a $Na/PO_4$ ratio that is above 3.0, a boiler is said to be operating with "equilibrium phosphate control." All three types of control can be attained and maintained with the instant invention.

With any of these corrosion control programs, the boiler uses phosphate as the major buffering agent. Additionally, sodium and phosphate concentrations are interdependent variables that must either be controlled simultaneously, or one subservient to the other. They cannot be controlled independently.

Furthermore, boiler systems are extremely slow systems because they comprise large volumes. As an example, a 280,000 pound water boiler having a blowdown rate of 3000 pounds/hour takes over three days to remove and replenish the boiler water. Many things can happen during that time that can alter the operator's initial guess at what concentrations should be added to manually correct control problems.

The applicants have found that conventional control schemes like Proportional Integral Derivative (PID) control are insufficient to provide practical, universally applicable automatic control of this boiler chemistry for a number of reasons. First, setpoint overshoot is a problem when attempting to control pH in a large volume system. Limitations in pumping capacity inherent in a real-life pumping scheme make "integral windup" a serious problem. Integral windup causes a control system to overshoot its setpoint. Overshoot is also a problem in controlling pH with PID control due to the asymmetric nature of pH control. Although this problem could potentially be avoided using blowdown flow controllers, these devices are expensive and difficult to maintain and calibrate.

Second, tuning such a PID loop is very difficult. Although tuning can be done in many ways, the methods generally require one of two sets of conditions be maintained, either of which are difficult to achieve in an operating boiler. In one general tuning method, the boiler chemistry must be held constant for multiples of the first order time constant defined by the volume of the boiler divided by its blowdown flow rate. In real-life applications, such a steady-state cannot be established for that length of time due to small perturbations in feedwater contaminants concentrations. In the other general tuning method, the boiler chemistry must be driven out of the region normally considered to be non-corrosive to derive the tuning constants. This negates the beneficial effect of the treatment. Since any change in blowdown flow rate (a normal part of boiler operations) will render the measured tuning constant invalid, tuning must be repeated for each blowdown flow setting.

There is one reference to sodium/phosphate control in the literature which demonstrates the difficulties of this method and its shortcomings. In "A Practical Approach to Real Time Data Acquisition and Automated Chemical Feed at a Fossil Fueled Cycling Duty Station", by C. E. Frederick presented at the *International Conference on Cycle Chemistry in Fossil Plants*, Jun. 4–6, 1991, the boiler system was tuned using a semi-empirical method to a specific boiler, rather than being adaptable to various types and sizes of industrial boilers. Furthermore, the system disclosed in that reference requires the use of phosphate analyzers which are expensive and require frequent re-calibrations and maintenance.

The closest art to automatically controlling the Na/PO$_4$ ratio in the water of an industrial boiler is in automated pH control systems. The control of pH is in itself a difficult task, as discussed in U.S. Pat. No. 5,132,916 (Gulaian et al.).

The following U.S. Patents disclose examples of automated pH control systems: U.S. Pat. No. 4,053,743 (Niemi), U.S. Pat. No. 4,239,493 (Niemi et al.), U.S. Pat. No. 4,181,951 (Boeke), U.S. Pat. No. 5,132,916 (Gulaian), U.S. Pat. No. 5,262,963 (Stana), U.S. Pat. No. 4,016,079 (Severin), U.S. Pat. No. 5,248,577 (Jerome), U.S. Pat. No. 4,033,871 (Wall) and U.S. Pat. No. 5,057,229 (Schulenberg).

The Niemi patent discloses an automatic system for controlling the pH and other concentration variables in a chemical reactor. However, use of that system would not be adaptable to an industrial boiler for the following reasons. The system utilizes a method that requires a steady state that is reached rapidly, which, as discussed previously, an industrial boiler does not exhibit. Consequently, the Niemi patent teaches controlling pH by use of a PID controller, which, as discussed previously, would be difficult to use in Corrosion Control Phosphate (CCP) programs described above.

The Niemi et al. patent discloses an automatic system for controlling the pH in a continuous flow vessel. However, this system is also not adaptable to industrial boilers for the following reasons. For boiler systems, the known tuning methods do not apply for the reasons described above. If the residence time distribution is known, then simulation of tuning methods requires a perfect match of a simulator and reality. The assumptions of linear processes of first order reactions is not applicable. Therefore, the method listed in Niemi et al. will only work for systems with small perturbations. Industrial boilers exhibit larger deviations. Furthermore, Niemi et al. identifies proportional, proportional-integral and proportional-integral-derivative controls along with an adjustable gain controller. Limitations on feed concentrations versus system volume will make any adjustable gain ineffective when bounded by limitations in a "pumpable region." Finally, the same pumpable limitations will make integral windup a serious problem in a large volume system.

The Boeke patent discloses an automatic control system for the adjustment of pH that is described using the term "on-off". However, this is not an ON/OFF controller. The series of solenoids that actuate flow across different size orifices produce a signal proportional to feedback. The series of solenoids provides proportional response that is discreet within a specific flow window. This is analogous to a stepwise integration of a continuous function.

The Gulaian patent discloses an automatic system for controlling pH and utilizing an estimation for a pH titration curve in the adaptive control of pH. However, this system is also relegated to short residence times and the use of proportional-integral control. Furthermore, the patent does not discuss limitations from integral windup.

The Stana patent discloses an automatic system for controlling a phosphoric acid plant. However, this system does not involve a model of the system but rather teaches a target feed where the system is compensated for its chemical deficit and then placed in steady state. The algorithm utilized by the system contains predetermined constants that are unique to a particular phosphoric acid plant, and are therefore, not readily adaptable to a variety of phosphoric acid plants (e.g., different plant volumes would require that new constants be calculated and inserted into the algorithm). Moreover, this system controls only sulfuric acid feed and does not try to control two interdependent variables.

The Severin patent discloses an automatic chlorine and pH control apparatus for swimming pools. The apparatus controls two variables, i.e., chlorine and pH, under the assumption that the two are not interrelated. Although chlorine affects pH, chlorine has a minor effect on pH and can be isolated and controlled separately. This is because in a swimming pool, chlorine is not the only buffering agent. Its contribution to the pH is masked by the high concentration of anions from the makeup water and atmosphere. This allows the pH to be controlled independent of the chlorine concentration. In contrast, as discussed earlier, a congruent controlled boiler uses phosphate as the major buffering agent, and the pH and phosphate are interdependent variables that must either be controlled simultaneously, or one subservient to the other. They cannot be controlled independently. In addition, the Severin apparatus also ignores the cycle time of a swimming pool and assumes that the control is constant through the system. It does not account for lag and residence time effects and probably cycles up and down drastically when in operation. Finally, the pH control range is anticipated as narrow, and works on the assumption that pH is linear in the chosen range.

The Wall patent discloses a system for continuously monitoring and controlling the pH and free halogen in swimming pool water. Although this patent mentions the concept of two-sided control (i.e., monitoring whether pH or halogen or both fall within or without predetermined ranges), the control of the pH of swimming pools and the control of pH in a boiler are not interchangeable, as described above.

The Schulenberg patent discloses an automatic system treatment of cooling circuit water. Although this system describes on/off pH control of a single component to provide one sided control and the system adds other components according to vaporous loss, the chemistry is different from that of a boiler. The chlorine in the Schulenberg patent is not the major buffer, and no attempt is made to maintain the $CO_2$ alkalinity. In addition, this system cannot control two interdependent variables. The corrosion inhibitor and the pH are not interdependent as are the phosphate (similar to a corrosion inhibitor) and pH.

The Jerome patent discloses a reactant concentration control method and apparatus for precipitation reactions. The system does base feed one reagent and adjusts the second. However, the method and apparatus assume that the system is near steady state at all times. The calculations are linearized and performed incrementally to make the calculations simpler. The model used in the method/apparatus is not a true continuously stirred tank reactor (as is the model for industrial boilers).

U.S. Pat. No. 5,141,716 (Muccitelli), which is owned by the same Assignee of the present patent application discloses a method of reducing corrosion in a boiler using coordinated phosphate control. However, this method calls for the administering of particular hydroxyethyl piperazines in specific ratios with phosphate, i.e., there is no automatic apparatus nor methods disclosed of conducting this feed.

Two other references which discuss coordinated phosphate control are: *Justification and Engineering Design for the On-Line Monitoring and Automation of a Congruent Phosphate/pH Program* by Michael E. Rogers, Ian Verhappen and Stephen Porter, Paper No. 413, The NACE Annual Conference and Corrosion Show 1992; *Expert System Helps Fine-Tune Boiler-Water Chemistry*, by Leyon O. Bretsel and Lon C. Brouse, Power Magazine 1987. In the former reference, although a proposal is discussed for controlling phosphate feed to the feedwater while controlling conductivity in the boiler water, there is no disclosure of any automatic simultaneous control of phosphate and congruency (Na/PO$_4$ ratio). With regard to the latter reference, although there is a discussion of providing the operator with chemical feed adjustments, there is no real-time, automatic control system that is disclosed for controlling the chemical pumps in order to control congruency.

Therefore the prior art does not disclose an effective method for controlling two interdependent and non-volatile chemicals, e.g., sodium and phosphate, in a multi-boiler system using a common feedwater line whereby each of the boilers are rarely at steady state. None of the above cited art have devised an apparatus nor a method for achieving an automatic coordinated sodium/phosphate control system for a variety of industrial boilers without the need to introduce separate feed pumps/feed lines for each boiler.

OBJECTS OF THE INVENTION

Accordingly, it is the general object of this invention to provide an automatic system for coordinated, equilibrium and congruent sodium/phosphate control for a plurality of industrial boilers fed by a common feed line which improves upon and overcomes the disadvantages of the prior art.

It is another object of this invention to provide an automatic system for sodium/phosphate control that requires no tuning procedure.

It is still another object of the preferred embodiment of this invention to provide an automatic system for sodium/phosphate control that can be implemented universally, that is easily adapted to a multiple boiler system that is fed from a common feedwater line.

It is yet another object of this invention to function as an advisory system, instructing the operator what to do, or to directly control congruency.

It is still yet another object of this invention to control any number of chemicals used in controlling congruency, e.g., polymer or chelant feeds as well as sodium and phosphate.

It is still yet a further object of this invention to control chemical concentrations when precipitation or volatilization is occurring.

It is still even a further object of this invention to control more than one boiler system simultaneously.

It is another object of this invention to provide an efficient method to achieve a common normalized congruency control (target) region of all of the boiler waters while minimizing the time spent outside of this control region by all of the boiler waters.

It is still yet a further object of this invention to provide an alternative means of determining the contribution to boiler water pH from ionic feedwater contaminant ingresses without having to use chemical analyzers and feedwater flow meters.

It is still a further object of this invention to provide a controller having a well-defined response for those situations where controllers using conventional general purpose equation solvers would simply conclude that there is no possible response.

It is further object of this invention to provide a chemical feed system which minimizes dead time while maximizing controllability.

SUMMARY OF THE INVENTION

These and other objects of the instant invention are achieved by providing an automatic control system and method for controlling at least two interdependent chemicals in the fluids of at least two continuously stirred tank reactors (CSTRs) linked in parallel by a common feedwater line and wherein each CSTR includes a respective blowdown flow and steam rate flow that define respective cycles for each of the CSTRs. In addition, a respective target region of the at least two interdependent chemicals is associated with each of the CSTRs and wherein each of the respective target regions is scaled according to the respective cycles of the CSTRs. The control system comprises input means for receipt of fluid parameters and control means responsive to the input means. Furthermore, the control means uses non-proportional control for automatically minimizing the time that said at least two interdependent chemicals in the fluids spend outside of a common normalized target region formed by the intersection of the respective target regions of the at least two CSTRs.

In addition, a second automatic control system and method is provided for controlling a respective sodium-to-phosphate ratio of at least two boiler fluids of respective industrial boilers that are fed through a common feedwater. The industrial boilers have respective blowdown flows and steam rate flows that define respective cycles for each boiler fluid. The system comprises input means for receipt of a boiler fluid parameter for each of the at least two boiler fluids and a parameter indicative of the cycles of each of the industrial boilers. Furthermore, the system comprises control means responsive to the input means for automatically driving the respective sodium-to-phosphate ratios of the at least two boiler fluids to a desired sodium-to-phosphate ratio region.

DESCRIPTION OF THE DRAWINGS

Other objects and many of the attendant advantages of this invention will be readily appreciated as the same becomes better understood by reference to the following detailed description when considered in connection with the accompanying drawings wherein.

DETAILED DESCRIPTION OF THE PREFERRED EMBODIMENT

Figure 1:
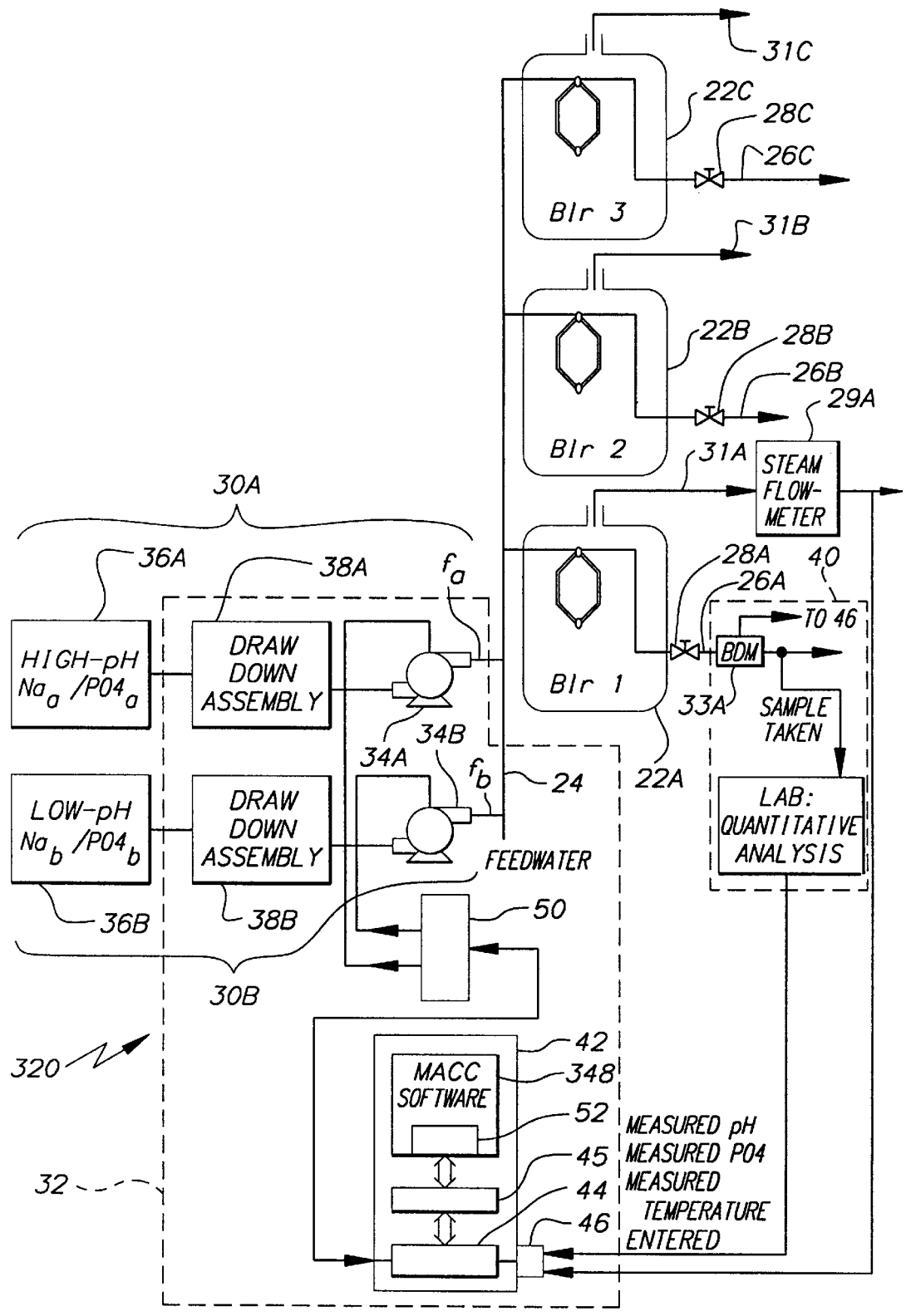
FIG. 1 is a block diagram of the Model Adaptive Congruent Control (MACC) system for use with multiple boilers.

Unless otherwise specified, all references to sodium or sodium-to-phosphate ratio (Na/PO$_4$) refer to that sodium which interacts with the phosphate to maintain the boiler water so as to inhibit corrosion. This is also referred to as "effective sodium" or the "effective sodium-to-phosphate ratio."

Referring now in detail to the various figures of the drawing wherein like reference characters refer to like parts, there is shown at 320 in FIG. 1, the preferred embodiment of the model adaptive congruent controller system of the present invention (hereinafter known as the MACC system). Generally, the MACC system 320 uses models of industrial boilers to predict the feed rates of particular mixtures of two chemicals, e.g., sodium and phosphate, to achieve and maintain an acceptable range of sodium-to-phosphate congruencies and phosphate concentrations where these congruencies are defined by the sodium-to-phosphate ratio being between high and low limits defined by the boilers' operating conditions, and then checks itself against its prediction and adapts its model to improve its control. The check is provided for by a laboratory pH and $PO_4$ analysis, rather than with the use of any on-line pH analyzers or $PO_4$ analyzers. Hereinafter, the targeted range of congruency and phosphate is referred to as the target region and the specific congruency and phosphate desired is referred to as the setpoint. Operation of the MACC system 20 for use with a single boiler is disclosed in application Ser. No. 08/321,338, now U.S. Pat. No. 5,696,696, which is incorporated by reference herein, and will not be discussed any further except with respect to the multiple boiler operation.

In particular, unlike the single boiler operation described in Ser. No. 08/321,338, now U.S. Pat. No. 5,696,696 the MACC system 320 requires the determination of the cycles for each of the boilers, i.e., the ratio of the total feedwater to the blowdown flow. Although there are many methods for determining the cycles for each boiler, the most common method employs the use of steam flowmeters for each boiler, as shown (only one 29A which is shown) in FIG. 1. However, it should be understood that the present invention 320 is not limited to the use of steam flowmeters. For example, instead of steam flowmeters, individual feedwater flowmeters (not shown) could be coupled to the individual feedwater inputs to every boiler; or, alternatively, both steam flowmeters and feedwater flowmeters could be used. The important point is that some method of determining the cycles for each boiler is required in the present invention 320.

Since the patentable distinction between the present invention 320 and the MACC system 20 of application Ser. No. 08/321,338 (now U.S. Pat. No. 5,696,696) resides not in the hardware (other than the use of multiple boilers, e.g., 22A–22C) but in the MACC software, the reference number 348 refers to the MACC software 48 of MACC system 20 but which also includes the multiple boiler algorithms discussed below.

As shown in FIG. 1, a plurality of industrial boilers, e.g., three (i.e., N=3, although the present invention is not limited to three) is shown by references 22A, 22B and 22C that are fed by a common feedwater 24 from a common feedpoint comprising feedstreams 30A and 30B. Each boiler has a respective steam output 31A, 31B and 31C, a respective blowdown flow 26A, 26B and 26C and a respective blowdown flow valve 28A, 28B, 28C; as with the MACC system 20, the MACC system 320 also does not control the blowdown flow of any of these boilers, although it should be understood the MACC system 320 could be operated where the boilers's cycles are fixed, i.e., their blowdown flows are controlled. The boilers may operate at different pressures with respect to one another.

It should be understood that in this parallel boiler configuration, the chemical feed affects all the boilers, i.e., there can be no independent boiler control. This is a real world configuration in that operators do not have the luxury of a separate feedwater line for each boiler but rather must couple multiple boilers to a single feed line. Thus, it is not an obvious modification of the MACC system 20 of Ser. No. 08/321,338 (now U.S. Pat. No. 5,696,696) to provide for such congruent control of multiple boilers from a single feedwater and the solution to this problem forms the subject matter of the present invention. The following discussion explains how the MACC algorithm can be implemented so as to provide the best possible congruent control to all the boilers 22A–22C simultaneously.

It is assumed that the information required to perform individual MACC control on each boiler, which includes regular pH and phosphate measurements for each boiler, is conducted in accordance with Ser. No. 08/321,338 (now U.S. Pat. No. 5,696,696); thus, each boiler has its own input means, similar to input means 40 for boiler 22A, for analyzing the respective blowdown flow 26A–28C and then providing such analysis data to the computer 42. In the present invention 320, the input means 40 also includes a blowdown flow meter (BDM) 33A that transmits a blowdown flow signal to the computer 42.

Next, if it is assumed that if all but one of the boilers were disconnected from the feedwater line, then the resulting single boiler system would be a good candidate for single boiler MACC control. Thus, from the point of view of optimizing the congruent control of the boilers involved, this invention can be viewed as providing an optimized congruent control for all the boilers, in the sense defined by the original MACC algorithm, subject to the additional constraints implied by the single, common feedwater line and feed point.

In general, these additional constraints can be expected to degrade control since, after all, there is no independent adjustment of the treatment feed rates into each boiler. However, there are certain special cases in which the control is no worse than if each boiler had had its own feed point. For example, a highly idealized system is assumed in which each boiler were physically identical in all respects, i.e., each had the same chemical concentrations, mass, blowdown flow rate, and feedwater flow rate (or equivalently, steaming rate), etc. Since all boilers would, by assumption, have the same pH and phosphate at all times, the single boiler MACC algorithm could be used to determine the appropriate feed rates into each of these boilers and then these feed rates could be multiplied by "N" to obtain the appropriate feed rates for the common, upstream, feed point. Somewhat more generally, it can be shown that if the characteristic times (ratio of boiler water mass to blowdown rate) and cycles (ratio of feed-water flow rate to blowdown flow rate) of all boilers are the same, then if any one of the boilers is chosen as the "lead boiler", the MACC-based feed rates are computed as usual for this boiler using:

(FractionOfTotalSteamIntoLeadBoiler)×($f_{amin}$, $f_{amax}$, $f_{bmin}$ & $f_{bmax}$), in lieu of $f_{amin}$, $f_{amax}$, $f_{bmin}$ & $f_{bmax}$ as in the single boiler in application Ser. No. 08/321,338, now U.S. Pat. No. 5,696,696.

If these single, lead boiler feed rates are then scaled up by a factor (FractionOfTotalSteamFlowIntoLeadBoiler)$^{-1}$ and used as the feed rates for the common feed point, all the boilers would, apart from startup transients, experience optimized control in the sense of defined by the MACC algorithm.

The preceding example, though an extremely special case, nonetheless illustrates the main idea of the present invention: exploiting the similarity of boilers exposed to a common feedwater line for control purposes. This similarity is a consequence of the basic mathematical structure of single boiler MACC control, as well as of the assumption that the concentrations in the feedwater entering each boiler are the same (e.g., that the feedwater is well-mixed before being split between the boilers). This similarity can be exploited to reduce the "boilers in parallel" control problem to a series of equivalent, coupled, single boiler MACC control problems, even when cycles and/or characteristic times of the boilers are different.

Similarity of the Boiler Systems in Parallel

From the point of view of single boiler MACC control, the control experienced by boiler systems in parallel is similar in that:

1) Under the assumption that treatment chemicals and contaminants are well-mixed in the common feedwater line before being split into separate feedwater lines for each boiler, the amount of feed and contaminant chemical flow into each boiler will be the same, apart from a scaling factor proportional to the fraction of the total, common, feedwater header flow that each boiler receives. In particular, note that the ratio of the sodium to the phosphate mass flow into all boilers will be the same;

2) The flow of chemical out of each boiler will be proportional to its blowdown flow rate; this is based on the non-volatility assumption of MACC control that all chemical flows out of the boiler are via the blowdown flow.

Figure 2:
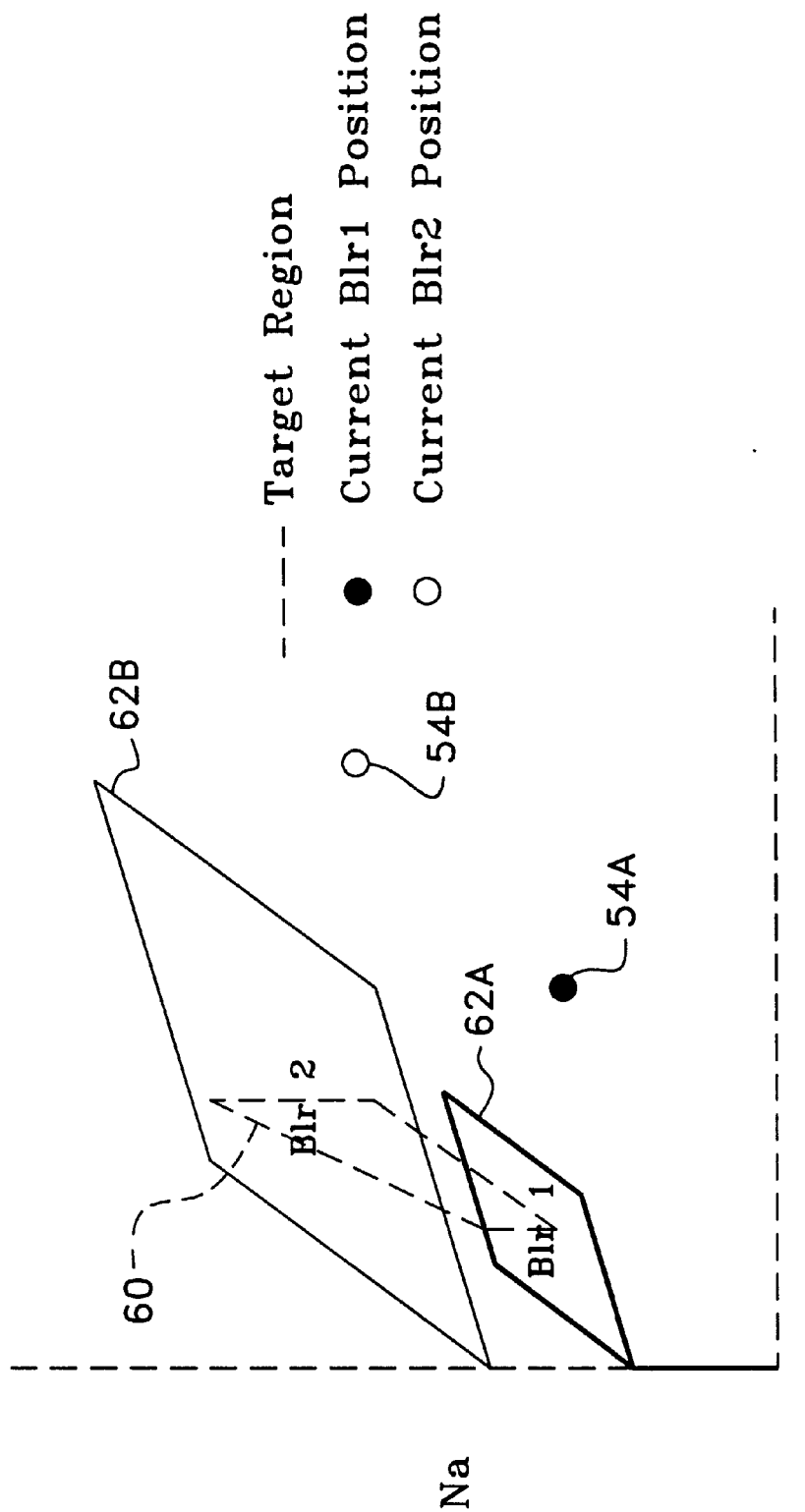
FIG. 2 is a boiler state space diagram showing the similarity of MACC pumpable regions for parallel boilers.

In the terminology of the MACC algorithm, the above facts imply that the MACC "pumpable region" (62A and 62B, FIG. 2, for boiler 22A (Blr 1) and boiler 22B (Blr 2)) for each of the boilers has the same shape apart from a scale factor which uniformly expands/contracts each of these pumpable regions relative to the others. This scale factor depends only on blowdown flow rate and the relative proportion of the total feedwater flow fed to each boiler (which in turn depends primarily on the relative steam load of each boiler). This can be seen mathematically from the steady-state concentrations equations (Equation #4 and #5 of application Ser. No. 08/321,338, now U.S. Pat. No. 5,696,696) that define the "pumpable region":

$$PO_4 = (f_a * PO4_a + f_b * PO4_b)/B \qquad \text{(Equation \#4)}$$

$$Na = (f_a * Na_a + f_b * Na_b + L)/B \qquad \text{(Equation \#5)}$$

If the above equations are repeated for each of the N boilers, the fact that feed flows ($f_a$, $f_b$) and contaminant flows (L) are all in the same relative proportions, and that blowdown flow rate (B) for each boiler divides every term on the right hand side of both equations, implies that the shape of each pumpable region 62A and 62B is the same apart from a scale factor, proportional to the ratio of the feedwater flow into the boiler divided by its blowdown flow rate. For example, in a two boiler system, if Blr1 gets ⅓ of the feed-water and Blr2 gets ⅔, and Blr1's blowdown flow rate is half that of Blr2, then the pumpable regions for both boilers are identical, since the common factor of two that multiplies all of the flow rates into Blr2 relative to those into Blr1 is exactly cancelled out by the factor of two arising in the denominator of Blr2's equations, due to its greater blowdown flow rate. Intuitively, in steady-state, the extra feed/contaminants are exactly cancelled by the extra blowdown. On the other hand, if relative feedwater flows were as before but instead both boilers had the same blowdown flow rates, then Blr1's pumpable region 62A would be scaled uniformly down by a factor or two, but otherwise shaped just like Blr2's pumpable region 62B, as shown in FIG. 2.

It should be noted that for simplicity, the target regions of Blr1 and Blr2 in FIG. 2 are assumed to be the same, indicated by target region 60; however, the methods described herein are just as appropriate where the target region for each boiler is different.

In FIG. 2, the MACC "target region" 60 has been superimposed on these pumpable regions 62A and 62B. Also shown are two points, 54A and 54B, representing the current concentrations of Blr1 and Blr2, respectively. These current concentration points have been deliberately placed at an ideal position: they are both in the same position relative to their corresponding pumpable region 62A and 62B. In other words, Blr2's current concentration point 54B is related to Blr1's current concentration 54A point by the same scale factor that relates points corresponding to the same feed rates in the two pumpable regions 62A and 62B. When this occurs, and in addition, the time constants of the boilers (Mass/BlowdownFlow) are the same, the similarity is complete, and not only the steady-state points but also the dynamic state-space trajectories will be similar.

If, in addition to this dynamic similarity, the ratio of feed-water flow rate to blowdown flow rate (e.g., the "cycles of concentration" for each boiler) were the same, then the pumpable regions 62A and 62B, as well as the dynamics of, both boilers would be the same. This extreme form of similarity makes it possible to use the "lead boiler" generalization of MACC, described in the previous section. Apart from startup transients which would die out exponentially in times proportional to the characteristic time of the boilers, all of these similar boilers would automatically experience optimized control in the sense defined by the MACC algorithm.

However, in the real world, the cycles and characteristic times of all boilers are not the same. How to incorporate such boiler-to-boiler differences, while still exploiting the basic underlying similarity of "boilers in parallel, is discussed below. Notwithstanding such generalizations, it is recommended that, in practicing this invention, the cycles and characteristic times of all boilers be adjusted to be as close to equal as possible: this minimizes the unavoidable degradation of control, relative to N independently controlled MACC boilers, experienced by the system as a consequence of the single feed point constraint.

The Common Normalized Target Region

When a specific combination of feed rates is fed for a long time, and assuming that over that time both the relative feed water flow and the blowdown flow rate of each boiler remain fixed, the resulting steady-state boiler concentrations reached in each boiler will be similar, i.e., in the same positions relative to their corresponding pumpable regions. Thus, a one-to-one correspondence between similar points in the pumpable regions of each boiler can be established.

The part of each such pumpable region 62A and 62B that intersects its corresponding target region 60 represents, for each boiler, the steady-state concentrations that are both in control and reachable via pump adjustments. In particular, (1) each target region 60 is intersected with its corresponding pumpable region 62A and 62B; and (2) both these variously clipped target regions and their associated pumpable regions are uniformly stretched so as to superimpose all of the pumpable regions 62A and 62B on each other, thereby forming a single pumpable region 71.

Figure 3:
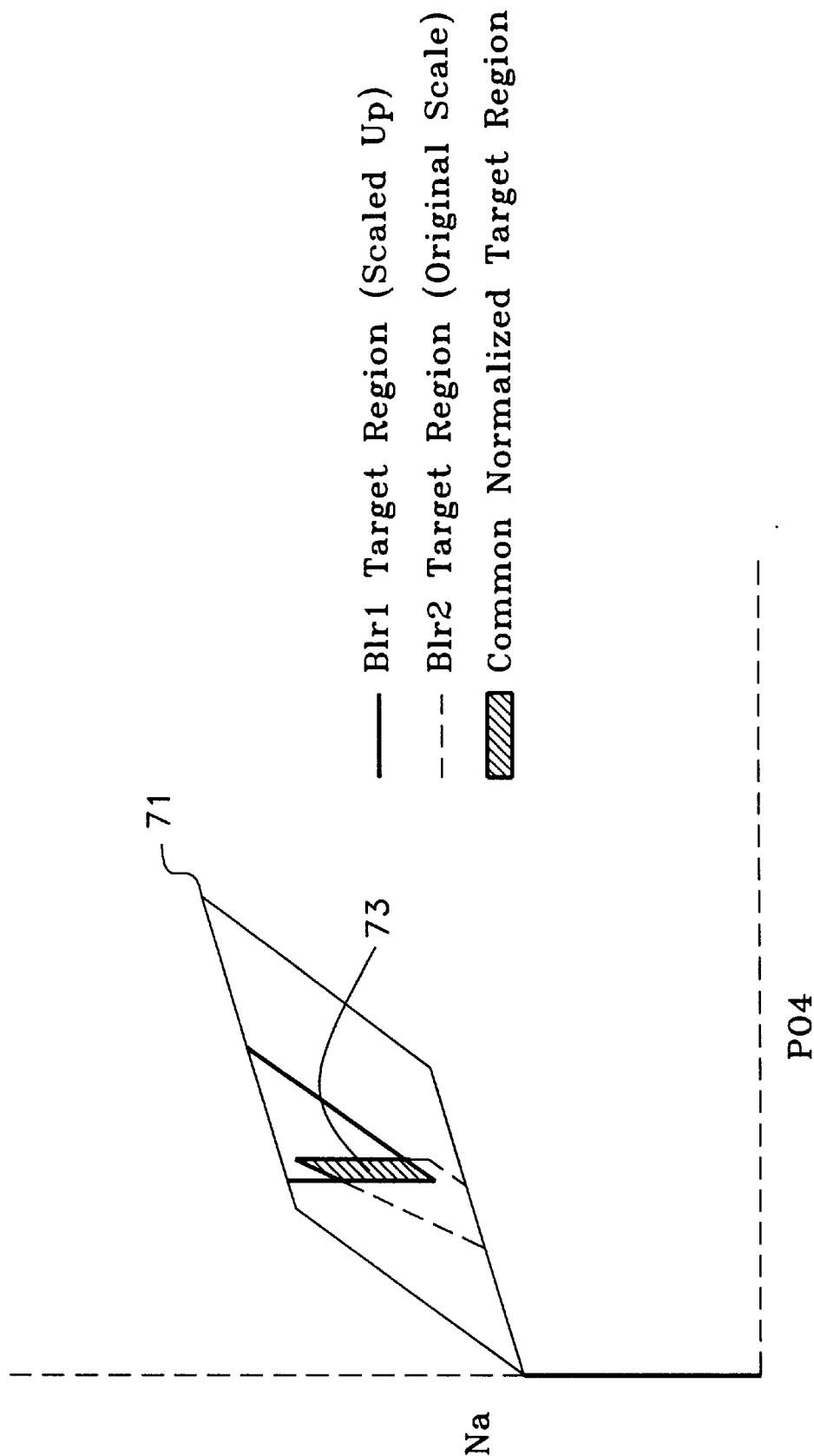
FIG. 3 is a boiler state space diagram showing the formation of a common normalized target region (CNTR)

The result of this process is shown in FIG. 3. FIG. 3 succinctly summarizes the one-to-one correspondence between points in the pumpable regions of the different boilers. In particular, FIG. 3 depicts the normalized form of the previous state space diagram (FIG. 2). The concentration axes (i.e., Na and $PO_4$) represent "normalized concentrations", concentrations relative to the range of steady-state concentrations corresponding to each boiler. Points in the common normalized target region 73 are both "pumpable" (correspond to steady-state points) and, if reached, imply every boiler is within its target region. Thus, if the chemical feed is maintained at these points, and nothing else changes, all boilers will be within their individual target regions when the final steady-state is reached.

A Control Scheme Based Directly on a Common Normalized Target Region (CNTR) Algorithm Once the common normalized target region (CNTR) 73 is established, the CNTR could be the basis of the following control method:

(1) Replace the single pumpable region 71 with the CNTR 73, which forms "an adjusted pumpable region";

(2) Using this adjusted pumpable region, which also is simultaneously the target region, perform MACC control on each boiler in turn;

(3) Of those boiler points that are not already in the CNTR 73, choose that stage one (see "stage one" defined in application Ser. No. 08/321,338, now U.S. Pat. No. 5,696,696) MACC adjustment that gets the next boiler into the CNTR 73 in the least time, and use its feed rates as the basis for the feed rate at the common feed point;

(4) Continue in this manner until all boilers are within the CNTR 73. Note that once in the CNTR 73, boilers will stay there, since a point in the CNTR 73 cannot be moved out of the CNTR 73 by feeding at a point within it (this follows because the CNTR 73 is an intersection of convex regions and, therefore, is itself convex; convex target regions are required by the original MACC algorithm).

(5) Stage two (see "stage two" defined in application Ser. No. 08/321,338, now U.S. Pat. No. 5,696,696) adjustments could use a nested target region for each boiler and then repeat stage 1 (step 3 above).

(6) The final stage feeds the centroid of the smallest common normalized target region into which all of the boilers can be placed at once.

One of the disadvantages of using the above approach (CNTR algorithm) is that it does not fully exploit the capabilities of the pumps 34A and 34B; if the CNTR 73 is small, then the rate of concentration adjustment will be slower than it needs to be. This problem can be somewhat alleviated by a nesting of target regions, using gross target regions that, (1) push the "problem boilers" into a broad control region quickly (and possibly push some boilers out of the narrower, true control region as a consequence, but never out of their gross target region);

(2) and then, once all boilers are at least within their gross target regions, the method proceeds as before with the narrower target regions.

Because the gross target regions are larger, a wider range of allowed pumping rates is obtainable, and therefore more aggressive control can be used during this initial period. A possible generalization would use scalable target regions for each boiler; hence, a conceptually infinite number of nested target regions. A discrete number of pre-defined target regions would be easier to program, and might provide nearly as good control; it also has the advantage of forcing the user to define the "emergency zone" and the "true target zone" for each boiler and the ability to raise specific alarms related to these specific user defined zones, which would presumably have a connection to the appropriate congruent control region for each boiler, based on its pressure.

Ultimately, however, restricting the pumpable region to the CNTR 73, though convenient in that it simplifies the algorithm, tends to make this approach more sluggish in its response to problems than it really needs to be. In the preferred approach, discussed next, this sluggishness can be overcome by using an algorithm that more aggressively exploits the full range of the pumpable region, and can be shown to be optimal in accordance with a reasonable definition of optimality for such systems. It should be noted that this preferred approach can still be used in conjunction with the nested target regions approach discussed above.

Common Normalized Pumpable Region (CNPR) Based Algorithm

Figure 4:
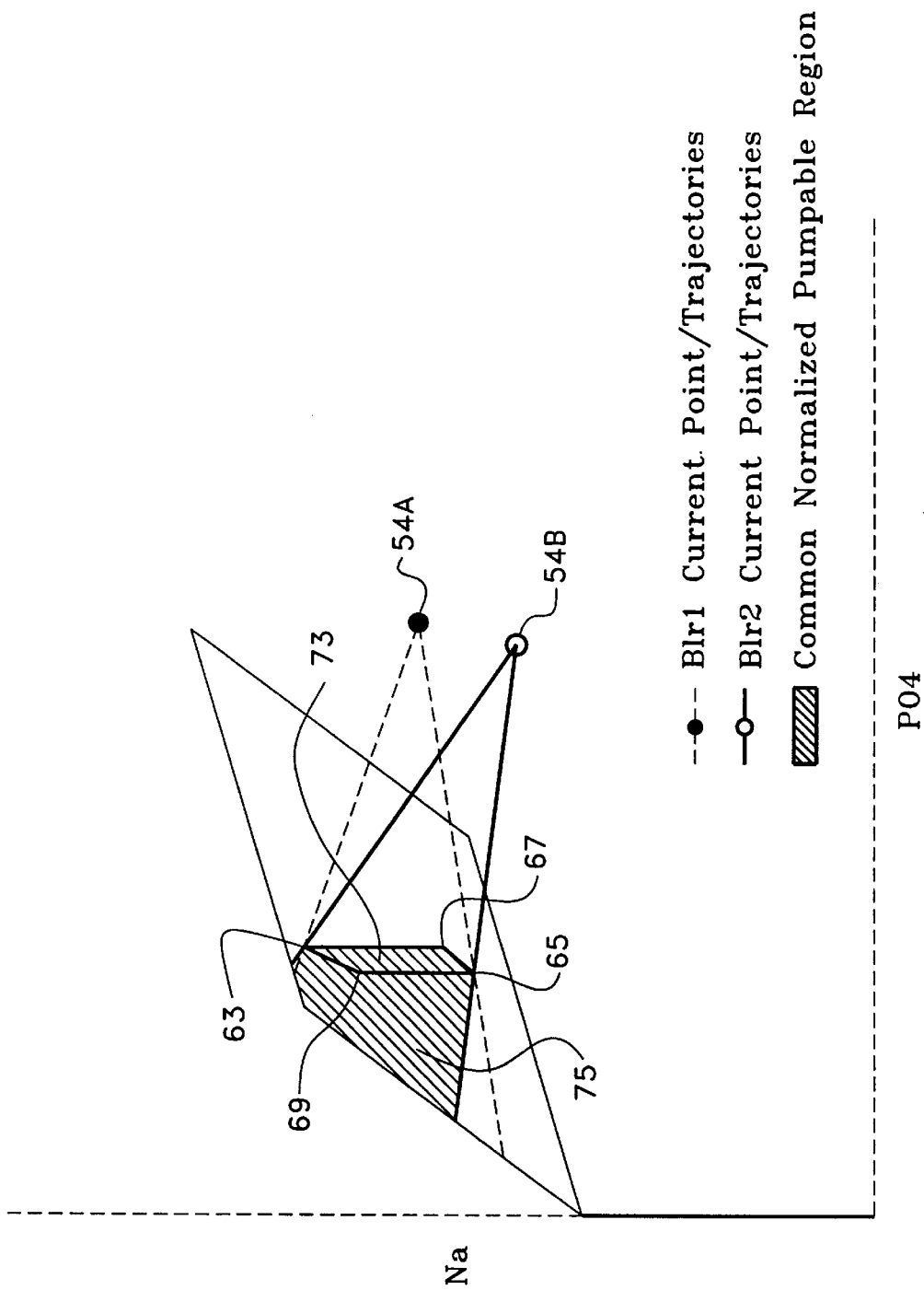
FIG. 4 is an enlarged boiler state space diagram of FIG. 3 showing the formation of a common normalized pumpable region (CNPR)

Consider, in the normalized space, the regions formed by the endpoints (on the single pumpable region 71) of all chemical feed trajectories that move a specific boiler into the previously defined CNTR 73. The intersection of all N such regions formed by considering each of the boilers in turn always contain (at least) the CNTR 73 described earlier. However, if the normalized points are, as shown in FIG. 2, in similar positions, then in general a much larger region of the intersection will be formed. This region of intersection is referred to as the "common normalized pumpable region" (CNPR 75), shown in FIG. 4. In particular, the CNPR 75 is established by projecting feedrate trajectories from the current boiler concentration to the extreme vertices (e.g., as shown in FIG. 4, extreme vertices 63 and 65 as opposed to inner vertices 67 and 69) of the CNTR 73 and beyond for every boiler. Thus, for each boiler, a region is formed by the endpoints of all trajectories that puts the particular boiler water into the CNTR 73. The region formed by the intersection of all such regions is defined as the common normalized pumpable region, CNPR 75. By construction, each point within the CNPR 75 moves every boiler closer to the common normalized target region, CNTR 73.

Figure 4A:
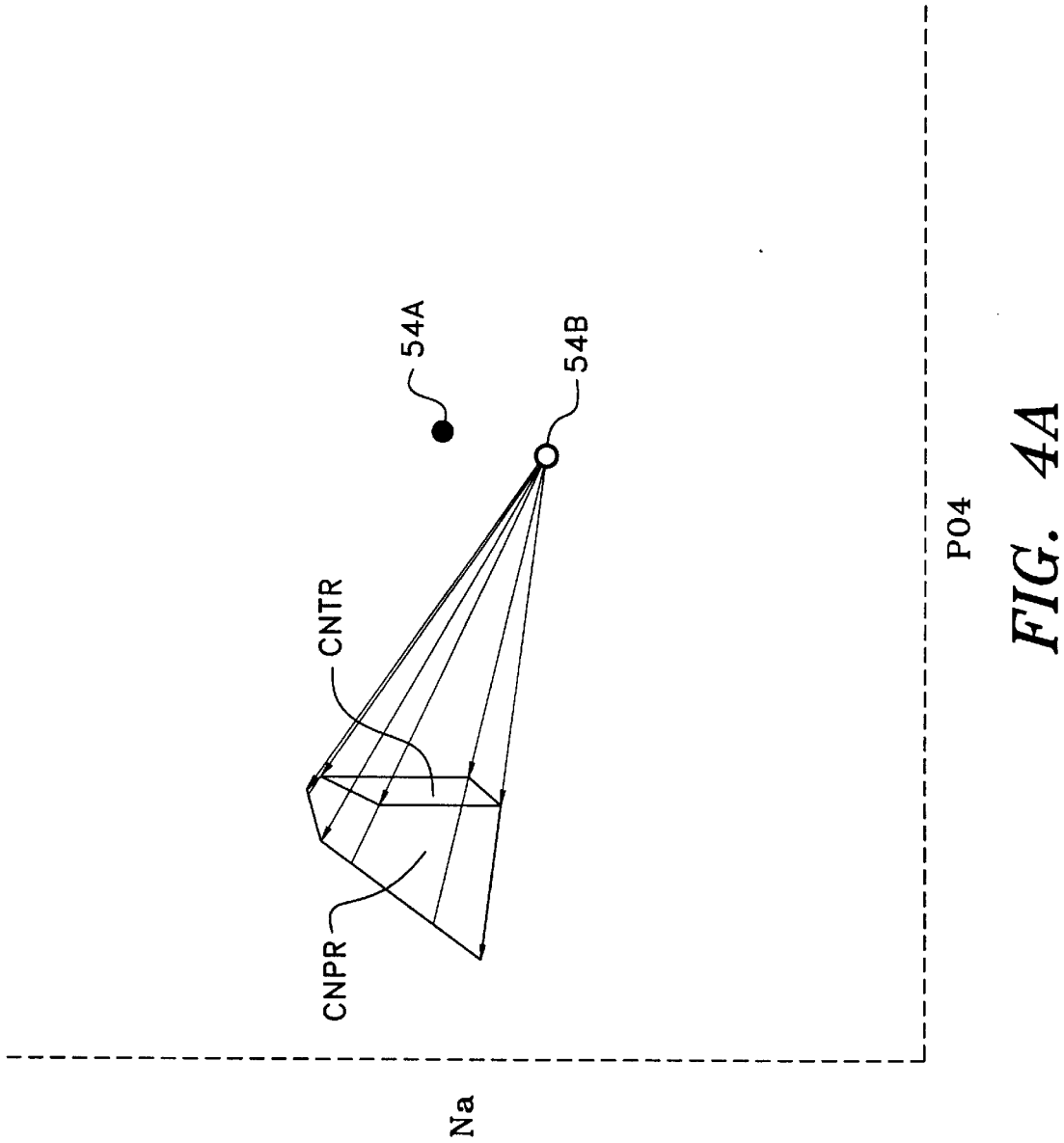
FIG. 4A shows the CNPR and CNTR of the boiler state space of FIG. 4 and a portion of the candidate shortest-time feedrate trajectories for boiler 2.

Once the CNPR 75 is established, the next step is to select that boiler whose optimal trajectory gets into the CNTR 73 first. This optimal trajectory then determines the initial feed rates into the common header shared by all of the boilers. The optimal trajectory is determined by calculating the stage 1 feedrates ($f_{a1}$, $f_{b1}$) and the associated stage 1 feed time ($d_{t1}$) for every boiler in accordance with application Ser. No. 08/321,338, now U.S. Pat. No. 5,696,696 for every boiler by substituting the CNTR 73 for the target region of application Ser. No. 08/321,338, now U.S. Pat. No. 5,696,696 and substituting the CNPR 75 for the pumpable region of application Ser. No. 08/321,338, now U.S. Pat. No. 5,696, 696 (see FIG. 4A). The optimal trajectory selected is that one which comprises stage 1 feedrates ($f_{a1min}$, $f_{b1min}$) having the minimum stage 1 feed time ($dt_{1min}$).

The next step is to determine the longest time, $dt_{MB}$ (where MB means "multiple boiler") to feed at the selected feedrates ($f_{a1min}$, $f_{b1min}$). This is accomplished by:

(1) constructing state space trajectories between each boiler's current boiler concentration point and the corresponding steady state point associated with the selected feedrates, $f_{a1min}$, $f_{b1min}$;

(2) for each such trajectory, determining the point at which the trajectory first intersects a CNTR 73 perimeter edge that does not contact the initial point of the trajectory; and then using the equations of application Ser. No. 08/321,338, now U.S. Pat. No. 5,696,696 to determine the time it takes for each boiler to reach its corresponding intersection point (if any);

(3) setting $dt_{MB}$ to the minimum of the times just computed; it should be noted that $dt_{MB} \leq dt_{1min}$.

Once $dt_{MB}$ is set, the feedstreams are then fed at the feedrates $f_{a1min}$, $f_{b1min}$ for either (1) $dt_{MB}$ or (2) the time it takes for new data to arrive, whichever is smaller.

With the first boiler "in" (i.e., in the CNTR 73), the computation repeats until all boilers are in the CNTR 73. Once any boilers are "in", the candidate trajectories made on other boilers are limited by the requirement that boilers already "in" cannot be pushed out again, as long as there is a CNPR 75. This limitation is a consequence of step 2, discussed above.

This scheme exploits the full range of the pumps 34A and 34B to greater advantage. When all the boilers are outside of the CNTR 73, by construction, each trajectory from any boiler's current point that ends within the CNPR 75 will cross into the CNTR 73. Since the one trajectory is selected, of all such trajectories, that gets one boiler into the CNTR 73 fastest, there is no possibility of overshoot of the other boilers-the boilers are moving in the correct direction too, only they take longer to reach the CNTR 73 than the "fastest" boiler (the "fastest" boiler could actually be the closest). And once at least one boiler is in the CNTR 73, the other boilers can be aggressively pushed into the CNTR 73 until the boilers already in the CNTR 73 "bump up against an edge of the CNTR 73," and more accurately, until such points are pushed into a "corner" of the CNTR 73. At that point, "the play in the system" has been exhausted and any further control reduces to the CNTR 73 algorithm, described in the previous section.

An important special case that the CNPR 75 algorithm handles well is the "slow boiler and the fast boiler." For example, it is assumed that one boiler has a very large characteristic time and another has a very small characteristic time, and they are both in the CNTR 75 when a sharp step in contaminants is observed. The fast boiler goes well-beyond its own target region but the slow boiler barely moves by the next time the operator enters the pH and PO4 for the boilers. Because the slow boiler moves so slowly inside the CNTR 73, the CNPR 75 algorithm essentially reduces to a single boiler MACC control on the fast boiler, since it properly recognizes the fact that such aggressive adjustments will get the fast boiler into line long before the MACC controller has a chance to push the slow boiler out of the CNTR 73. By contrast, the first, CNTR 73 algorithm would not have exploited this "inertial advantage" of the slow boiler so aggressively and, as a result, the fast boiler would have been out of control much longer than it needed to be.

As a summary, the method for moving into the CNTR 73 is:

1) find the fastest trajectory into the CNTR 73;
2) determine how long to feed at that fastest rate which is determined by the shortest of either,
   (a) which boiler water gets in first; or
   (b) which boiler water gets pushed to the edge of the CNTR 73 that it is not already on.

In particular, this preferred MACC multi-boiler algorithm is given by:

(1) If (new data is available) then {
   a) update each boiler's state space (the "scale the map" of application Ser. No. 08/321,338, now U.S. Pat. No. 5,696,696) and state space point to reflect new measurements;
   b) recompute the CNTR 73 to reflect these updates;
   c) define InnerCNTR as a region nested within CNTR 73. Note that if InnerCNTR is defined as a region consisting of a single point, the centroid of the CNTR 73, then subsequent controller actions that use InnerCNTR as ActiveCNTR will, in the single boiler case, correspond to stages 2 and 3 of application Ser. No. 08/321,338, now U.S. Pat. No. 5,696,696.}

(2) If (all boiler state space points within CNTR) then
   ActiveCNTR=InnerCNTR
else
   ActiveCNTR=CNTR (3) Recompute the CNPR using ActiveCNTR in lieu of CNTR. (Note that, for purposes of this calculation, any boilers on the perimeter of the ActiveCNTR are treated as if they are just outside of the ActiveCNTR. This helps to incorporate the constraint that boilers already in the ActiveCNTR should not be pushed out again.)

(4) For each boiler outside of the ActiveCNTR, compute the stage 1 feed rates and stage 1 time, $d_{t1}$, as described in application Ser. No. 08/321,338, now U.S. Pat. No. 5,696,696, but where ActiveCNTR and CNPR are used in lieu of the ordinary target region and pumpable region. Of the up to N such stage 1 feedrates, choose those stage 1 feedrates ($f_{a1min}$, $f_{b1min}$) which have the minimum associated stage 1 feed time, $dt_{1min}$.

(5) Determine the longest time, $dt_{MB}$, to feed at these rates by:
   (a) constructing state space trajectories between each boiler's current point and the corresponding steady state point associated with the ($f_{a1min}$, $f_{b1min}$) of step 4.
   (b) for each such trajectory, determining the point at which the trajectory first intersects an ActiveCNTR perimeter edge that does not touch the initial point of the trajectory. Use the equations of application Ser. No. 08/321,338, now U.S. Pat. No. 5,696,696 to determine the time it takes for each boiler to reach its corresponding intersection point (if any).
   (c) set $dt_{MB}$ to the minimum of the times computed in (b) above.

Note that $dt_{MB} \leq dt_{1min}$.

(6) Feed at the feedrates ($f_{a1min}$, $f_{b1min}$) determined in step 4 for the smaller of:
   (a) the time $dt_{MB}$ computed in step 5;
   (b) the time it takes for new data to arrive.

Advance each boiler's state space point along its state space trajectory an amount consistent with feeding for this length of time, using the equations of application Ser. No. 08/321,338, now U.S. Pat. No. 5,696,696.

(7) Go to Step 1.

It should be noted that the steps above are defined with just two nested target regions: CNTR and InnerCNTR. The above is easily generalized to employ a sequence of nested target regions, CNTR, InnerCNTR$_i$ for i=1, 2, . . .

The use of a common normalized target region (CNTR) focuses on getting all boilers into a jointly sustainable part of their target regions. The term "jointly sustainable" is defined by the condition that if the current cycles and characteristic times for each boiler were to remain in effect indefinitely, then all boilers could be kept within their respective target regions indefinitely as well. In other words, it is not enough to have all boilers in control now, but it is desirable to place them into a position in which, if nothing else changes, all of them can be simultaneously maintained in control forever.

Given this concept of jointly sustainable target regions, the multi-boiler generalization of MACC control described in the preceding section is optimal if the criterion for "best" control is defined as follows:

At each point in time, minimize the time required to get one more of the out-of-control boilers into a jointly sustainable part of its target region, subject to the constraints that:

1) all boilers already in a jointly sustainable part of their target region are never pushed out of it, and
2) all boilers not yet in the jointly sustainable part of their target region are at least always moved closer to it.

This optimality criterion agrees with the common sense notion that it is desirable to bring an out of control boiler into its target region as quickly as possible, provided that such aggressive adjustment does not result in pushing any of the other boilers out of their target regions, or in pushing any other out-of-control boilers even further away from their target regions.

Figure 5:
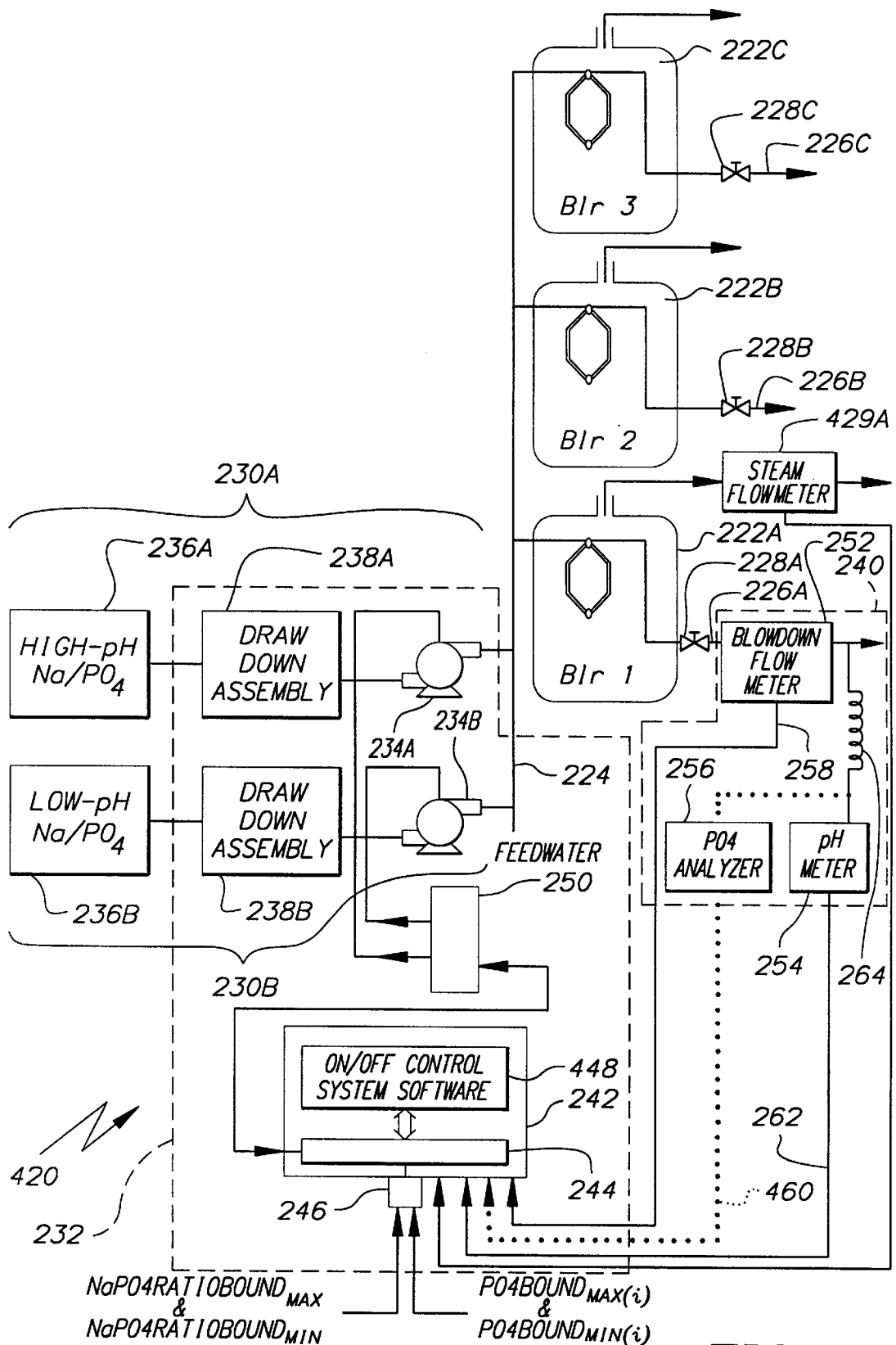
FIG. 5 is a block diagram of the ON/OFF control system for use with multiple boilers.

There is shown in FIG. 5 a second embodiment of an automatic congruent controller system 420, hereinafter known as the ON/OFF control system 420. As with the MACC system 320, the ON/OFF control system 420 controls two interdependent variables, namely, phosphate and sodium, the latter by way of monitoring the pH.

As stated earlier with respect to the MACC system 320, all subsequent references to sodium and/or to the sodium-to-phosphate ratio ($Na/PO_4$) of the boiler water refers to that sodium which interacts with the phosphate to maintain the boiler water so as to inhibit corrosion. This is also referred to as the "effective sodium" or the "effective sodium-to-phosphate ratio."

As discussed in detail in application Ser. No. 08/321,338, now U.S. Pat. No. 5,696,696, which is incorporated by reference herein, the ON/OFF control system 220 is arranged to control water treatment chemicals to be introduced into a single boiler 222. The boiler 222 has an effluent flow (hereinafter known as blowdown flow 226) and a blowdown valve 228. The ON/OFF control system 220 does not control the blowdown flow 226 via the blowdown valve 228. In fact, one of the distinguishing features of the ON/OFF control system 420 over conventional boiler fluid control systems is that the blowdown flow 226 can be varied independently of the ON/OFF control system 420. However, it should be understood that the ON/OFF control system 420 of the present invention can also operate where the boilers' cycles (discussed next) are fixed, i.e., their blowdown flows are controlled.

Furthermore, unlike the single boiler operation described in Ser. No. 08/321,338, now U.S. Pat. No. 5,696,696, the ON/OFF control system 420 requires the determination of the cycles for each of the boilers, i.e., the ratio of the total feedwater to blowdown flow. Although there are many methods for determining the cycles for each boiler, the most common method employs the use of steam and blowdown flowmeters for each boiler, as shown (only one 429A which is shown) in FIG. 1. However, it should be understood that the present invention 420 is not limited to the use of steam flowmeters. For example, instead of steam flowmeters, individual feedwater flowmeters (not shown) could be coupled to the individual feedwater inputs to every boiler. The important point is that some method of determining the cycles for each boiler is required in the present invention 420.

Since the patentable distinction between the present ON/OFF control system 420 and the ON/OFF control system 220 for use with a single boiler resides not in the hardware (other than the use of multiple boilers, e.g., 222A–222C) but in the ON/OFF control system software, the reference number 448 (FIG. 5) refers to the ON/OFF control system software 248 of ON/OFF control system 220 but also includes the multiple boiler algorithms discussed below.

Figure 6:
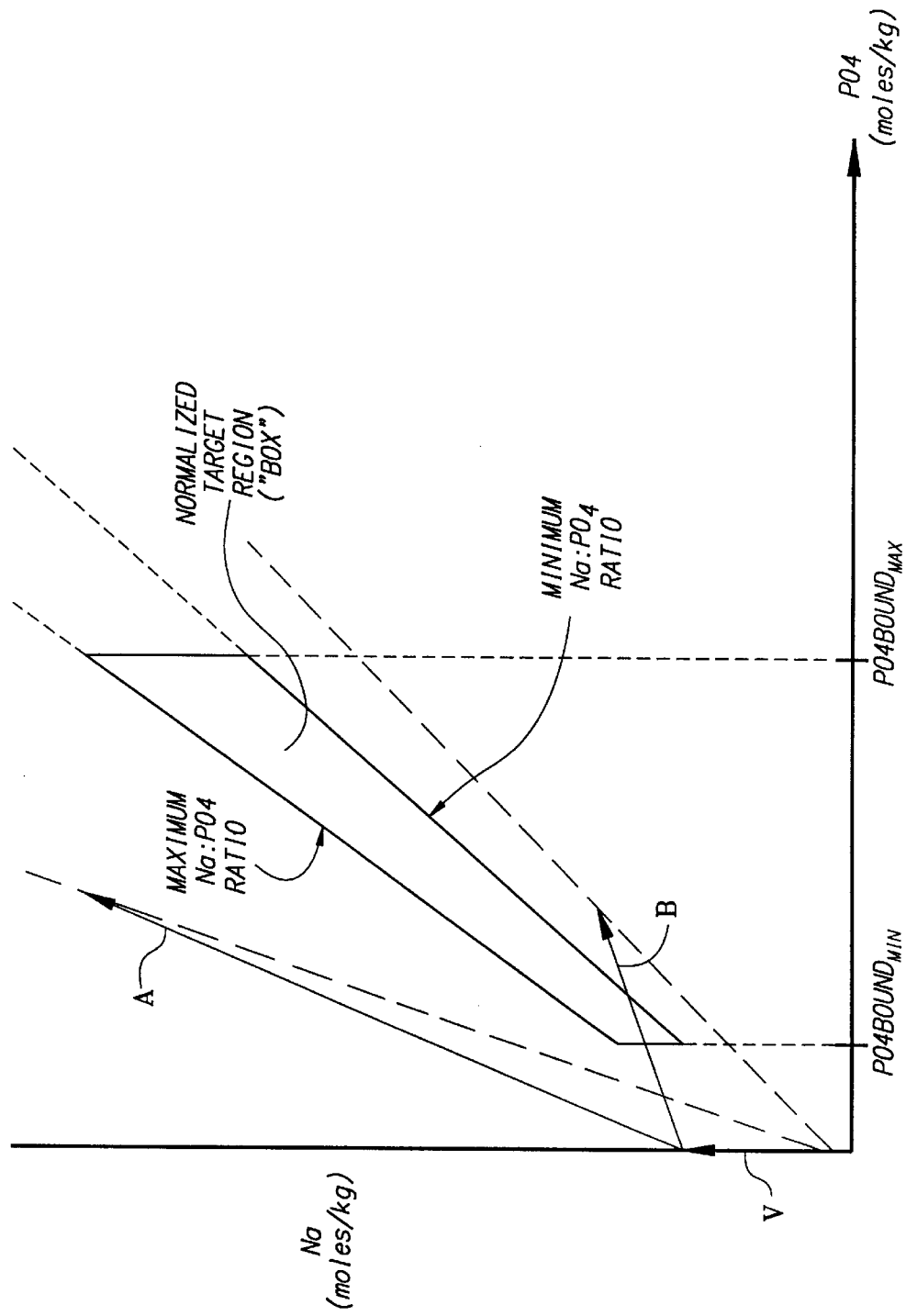
FIG. 6 is the boiler state space diagram for multiple boilers using a common feedline with ON/OFF control, and assuming similar upper and lower phosphate control limits among all of the boilers.

The ON/OFF control system 420 basically comprises a first chemical feedstream 230A, a second chemical feedstream 230B, a control means 232 and an input means 240. The first chemical feedstream 230A and the second chemical feedstream 230B are each connected to the common feedwater line 224. The first chemical feedstream 230A is arranged to deliver a first fluid treatment material or chemical, e.g., a sodium phosphate mixture having a particular sodium-to-phosphate ratio and a known phosphate concentration, to the water in the boilers 222A–222C. Similarly, the second chemical feedstream 230B is arranged to deliver a second fluid treatment material or chemical, e.g., a sodium phosphate mixture having a particular sodium-to-phosphate ratio and a known phosphate concentration to the water in the boilers 222A–222C. It is important to note at this juncture that the sodium-to-phosphate ratio in the first chemical feedstream 230A must be different from the sodium-to-phosphate ratio in the second chemical feedstream 230B while the respective known phosphate concentrations in the feedstreams can, in certain circumstances, be identical. The particular sodium-to-phosphate ratio ($Na/PO_4$) determines a particular pH for that fluid treatment material. Where the known phosphate concentration ($PO_4$) in both feedstreams is identical, then the different sodium concentrations (Na) in each feedstream determine the pH (high or low) of each fluid treatment material. The importance of the pH is that the pH of the boiler water, at a fixed phosphate concentration, is indicative of the sodium concentration in the boiler waters. Thus, monitoring the pH of the boiler waters provides an effective method of monitoring the sodium-to-phosphate ratio of the boiler waters and then in determining which of the two feedstream sodium phosphate mixtures is to be fed to the boiler waters to adjust the sodium-to-phosphate ratio of the boiler waters, as will be described below. As shown in FIG. 6, by fixing the amount of phosphate in the boilers 222A–222C, varying the amount of sodium permits the sodium-to-phosphate ratio of the boiler waters to be controlled.

Further details as to the operation of the ON/OFF control system are set forth in application Ser. No. 08/321,388, now U.S. Pat. No. 5,696,696, and will not be discussed any further except with respect to multiple boiler operation. It should be understood that the single blowdown flow 226 and blowdown valve 228 of ON/OFF control system 220 have been replaced with blowdown flows 226A–226C and blowdown valves 228A–228C. Although only one input means 240 is shown in FIG. 5, it should be understood that each boiler 222A–222C has its own input means 240.

In the system 420, the steady-state phosphate associated with either feed tank 236A or 236B, and the steady-state sodium concentrations associated with the high and low Na:PO4 ratio feed tanks 236A and 236B are given, for the "ith" boiler, by:

PO4(i)=FeedRate*FeedPO4* Cycles(i)/Total FeedWater (for both tanks/feed tanks)

$Na_{High}$(i)=($L_{Na}$+FeedRate*NaPO4Ratio$_{High}$*FeedPO4) *Cycles(i)/TotalFeedWater $Na_{Low}$(i)=($L_{Na}$+FeedRate*NaPO4Ratio$_{Low}$*FeedPO4) *Cycles(i)/TotalFeedWater Here FeedRate is the flow rate from the currently selected feed tank, FeedPO4 the phosphate concentration in the feed tanks (for simplicity, as with single boiler ON/OFF, assumed to be the same in both tanks), NaPO4Ratio$_{High}$ and NaPO4Ratio$_{Low}$ are the Na:PO4 ratios of the two chemical feed tanks 236A and 236B, TotalFeedWater is the feed water flow rate in the common, shared, feed water header, L$_{Na}$, is the total sodium leak (feedwater contaminant ingress) into the shared feedwater header, and Cycles(i) is the instantaneous cycle given by the ordinary definition of boiler cycles for the "ith" boiler:

Cycles(i)=(Steam(i) +Blowdown(i))/Blowdown(i)

Noting that (Steam(i)+Blowdown(i))/TotalFeedWater is the fraction of the total feedwater (and hence, of treatment chemical and contaminant) that flows into each boiler, the above equations are a consequence of the assumed nonvolatility of the treatment chemicals and contaminants, the assumed "good mixing" in the common feedwater line, and the application of mass balance around each boiler.

The important point to note about the above equations is that each boiler's steady-state concentrations are the product of a value which is the same for all of the boilers and the cycles of each boiler. Based on that, FIG. 6 depicts the possible steady-state feed-rates associated with each of the boilers sharing a common feed water line, and using an ON/OFF pumping configuration into that line.

The vertical vector, V, represents the steady-state, contaminant determined, effective sodium levels associated with one of the boilers (i.e., the Na concentration, if both high and low NA:PO4 ratio tanks 236A and 236B, respectively, were turned off for a long time). The vector A represents the increase in steady-state concentrations, beyond those from the contaminant, associated with feeding from the high Na:PO4 ratio tank 236A; the vector B, the corresponding increase associated with feeding, instead from the low Na:PO4 ratio tank 236B. It should be understood that FIG. 6 depicts an ON/OFF control system whereby the feed tanks 236A and 236B contain the same concentration of phosphate, which is why the PO4 component of both of these vectors is the same; however, as stated earlier, it is not necessary that both tanks contain the same amount of PO4.

The two dotted lines, on the other hand, represent all of the various steady-state concentrations that could be associated with feeding from either tank to any other boilers that might be present in the system 420, each with possibly different cycles of concentration. For example, if a boiler's cycles were half that of the original boiler whose vectors are shown, then, all else being equal, the corresponding steady-state concentrations for high and low Na:PO4 ratio feed would be half the distances along each dotted line, measured from the origin, as they were for the original boiler whose vectors are shown; a boiler with double the cycles would have its two corresponding steady-state concentrations along the same dotted lines, only twice as far from the origin, as for the original boiler, etc.

In general, since all steady-state equations for the boiler s differ only via the multiplicative factor of Cycles(i), the steady-state concentrations for all boilers lie on the dotted lines shown in the FIG. 6. In addition, since both tanks 236A and 236B have the same phosphate concentrations, each boiler's high and low Na:PO4 ratio steady-state concentrations will be on the intersection of a vertical line, corresponding to the steady-state phosphate for that boiler, with these two dotted lines.

It should be noted that if the target region does not overlap the region between the dotted lines, maintaining congruency is impossible.

Maximum Cycle-Ratio Based Phosphate Control

Given the Cycles(i) for each boiler, the next step is to choose that FeedRate such that all of the steady-state PO4( i) are between PO4Bound$_{min}$ and PO4Bound$_{max}$, where these two values are predetermined and loaded into the ON/OFF controller 242. PO4Bound$_{min}$ and PO4Bound$_{max}$ are predetermined values that depend basically on the operating pressure of the boilers and are inputted to the ON/OFF controller 242 by the operator. The following discussion assumes that PO4Bound$_{min}$ values for each boiler and the PO4Bound$_{max}$ values for each boiler are the same. However, as will be discussed later, the ON/OFF control system 420 is also designed to operate where these values are different for each boiler, i.e., PO4Bound$_{min(i)}$ and PO4Bound$_{max(i)}$.

One way to choose the particular Feedrate is to choose that feedrate such that the range between the lowest PO4(i) and the highest PO4(i) is centered in the middle of the phosphate control limits of the CPPC target region (between PO4Bound$_{min}$ and PO4Bound$_{max}$). That is, a FeedRate is sought such that:

PO4Bound$_{Min}$<=PO4(iMin) and PO4(iMax)<=PO4Bound$_{Max}$ and

PO4(iMin)-PO4Bound$_{min}$=PO4Bound$_{max}$-PO4(iMax)

Here PO4(iMin) is the smallest steady-state boiler concentration and PO4(iMax) the largest (which correspond to the boilers with the smallest and largest cycles, as per the above equations for PO4(i)). Substituting the equation for the steady-state phosphate concentration, PO4(i), into the last equation above and solving for FeedRate:

FeedRate=(TotalFeedWater/FeedPO4)*(PO4Bound$_{max}$+ PO4Bound$_{min}$)/(Cycles(iMax)+Cycles(iMin))

As a check, note that when the cycles in all of the "N" boilers are equal and have equal blowdown flow rates, this equation reduces to the expected result that "N times more" feed is needed to attain the midpoint of the control range than is required for just one such boiler.

By feeding at this rate, the average of the steady-state PO4 concentrations of the highest and lowest cycle boilers will, over a period of time, be right in the middle of the control range for phosphate. And, provided it is possible to maintain all of the boilers within their control range, this will also guarantee that these two boilers' steady-state PO4 concentrations, and, therefore, every other boiler's steady-state concentrations (which also lie between these two limits), will lie within the control range as well. In general, it will be possible to retain, in steady-state, all of the boiler steady-state concentrations within their control range provided that:

Cycles(iMax)/Cycles(iMin)<=PO4Bound$_{Max}$/PO4Bound$_{Min}$, where Cycles(iMax) represents the maximum instantaneous cycle of all of the boilers and Cycles(iMin) represents the minimum instantaneous cycle of all of the boilers;

On the other hand, if this condition is violated for an extended period, phosphate control with such a control system will be impossible.

The above condition is a consequence of the two phosphate limit based inequalities and the equation for steady-state phosphate give above. This upper bound on the ratio of cycles between any two boilers is referred to as "the maximum cycles ratio" for the system. The controller shoul raise a warning whenever this maximum cycles ratio is exceeded, since it means that if current conditions were to continue indefinitely, keeping phosphate in the box for all of the boilers would be impossible. In particular, if the cycles ratio equals the maximum cycles ratio then the minimum and maximum steady-state concentrations, PO4(iMin) and PO4(iMax), will exactly equal PO4Bound$_{Min}$ and PO4Bound$_{Max}$, making it just barely possible to keep all of the boilers within their phosphate bounds. Note that in general, iMax and iMin (the indexes of the boilers with the maximum and minimum cycles) will vary depending upon load swings, blowdown adjustments, etc.

In special cases, the maximum and minimum cycles for some or all boilers would be known in advance. Consider, however, the general case in which the Cycles(i) for each boiler is allowed to vary freely (either due to load swings or blowdown flow adjustments) so long as the maximum cycles ratio constraint given above is not violated. As long as the feed rate is constantly updated to reflect the most recently computed maximum and minimum cycles, and as long as the above constraint is never violated, one can show that, apart from start-up transients or violations of the assumptions of the basic CSTR model (e.g., the presence of PO4 not from the feed tanks), the PO4 levels for all boilers will always remain within their control limits as well.

For example, suppose that the control limits on phosphate are 10 ppm (PO4Bound$_{Min}$) to 30 ppm (PO4Bound$_{Max}$), thus implying a maximum cycles ratio of 3. Suppose that, initially, a fixed cycles boiler (i.e., a boiler that comprises a controller, not shown, that maintains the boiler at a fixed cycle) is being operated at 30 cycles and a variable cycles boiler at 90 cycles, which would put the steady-state concentrations at 10 and 30 ppm, respectively, if the feed rate formula given had been used. If the variable cycle boiler suddenly dropped to 10 cycles, the feed rate formula implies that the steady-state phosphate concentrations of both boilers would be interchanged, and, as both boilers assumed their new positions at opposite ends of the phosphate control range, they would pass through intermediary phosphate levels, all of which would also be within the control range. In general, as long as the current steady-state phosphate concentrations and the projected steady-state concentrations are in the control range, phosphate will be maintained within that range as well. The selection of the feedrate as per the above equation guarantees that these conditions, apart from possible transients, uncharacterized sources or sinks of phosphate, etc., will be satisfied.

The above maximum cycle-ratio based phosphate control was discussed under the assumption that the phosphate bounds for the particular boilers are identical, i.e., PO4Bound$_{min(1)}$=PO4Bound$_{min(2)}$=. . . PO4Bound$_{min(n)}$=PO4Bound$_{min}$ and
PO4Bound$_{max(1)}$=PO4Bound$_{max(2)}$=. . . PO4Bound$_{max(n)}$=PO4Bound$_{max}$.

Figure 7:
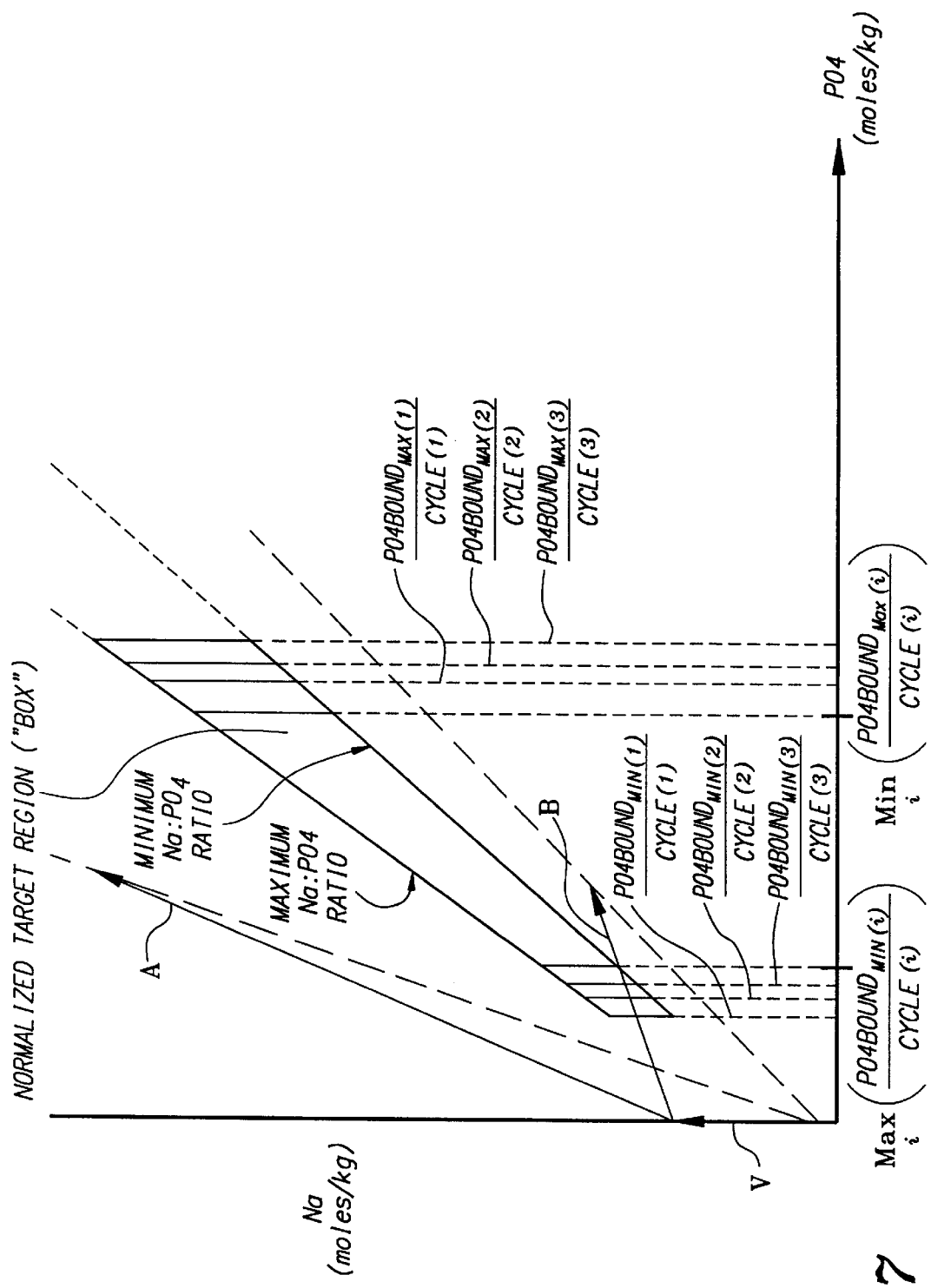
FIG. 7 is similar to FIG. 6 but depicting multiple boilers (e.g., three) having respective upper and lower phosphate control limits.

However, a more generalized form of the phosphate control can be made where the phosphate bounds for the particular boilers are different, as shown in FIG. 7.

To that end, under the assumption of a steady-state condition, the chemical concentration in the ith boiler, PO4(i), is given by the following equation:

PO4(i)=FeedWater(i)*FeedPO4conc/Blowdown(i)   (a)

where FeedPO4 conc=Total Feed PO4/Total FeedWater.
This equation can be used to back calculate the proper FeedPO4 conc. As a result, to maintain PO4(i) within its minimal bound PO4Bound$_{min(i)}$, and maximal bound PO4Bound$_{max(i)}$ the FeedPO4conc should be in between:

FeedPO4concmin(i)=PO4Bound$_{min(i)}$*Blowdown(i)/FeedWater(i)=PO4Bound$_{min(i)}$/Cycle(i)   (b)

and

FeedPO4concmax(i)=PO4Bound$_{max(i)}$*Blowdown(i)/FeedWater(i)=PO4Bound$_{max(i)}$/Cycle(i)   (c)

This gives an interval for FeedPO4conc to ensure that PO4(i) is under control. It is thus apparent that in order to have all PO4(i) under control, it is necessary to have all intervals determined by equations (b) and (c) fall within a common interval, i.e.,:

max(FeedPO4concmin(i))≦min(FeedPO4concmax(i)).   (d)

Under this condition, any value of FeedPO4conc in the interval bounded by the above inequality will keep all boilers in their control regions for PO4. Thus, the generalized form of this phosphate control can be written:

FeedPO4conc=a*max(FeedPO4concmin(i))+(1−a)*min(FeedPO4concmax(i))   (e)

where 0≦a≦1. The default value of a is 0.5.

In the special case, where all PO4Bound$_{min(i)}$ are equal, and all PO4Bound$_{max(i)}$ are equal, inequality (d) can be simplified as (using equations (b) and (c)):

$$\max(\text{PO4Bound}_{\min(i)} / \text{Cycle}(i)) \le \min(\text{PO4Bound}_{\max(i)} / \text{Cycle}(i)) \quad (f)$$

$$\Rightarrow \max(\text{PO4Bound}_{\min} / \text{Cycle}(i)) \le \min(\text{PO4Bound}_{\max} / \text{Cycle}(i))$$

and using the principles that:

$$\max(k \cdot b_i) = k \cdot \max(b_i), \text{ where } k \text{ is a constant; and}$$

$$\max(1/b_i) = 1/\min(b_i)$$

$$\Rightarrow \text{PO4Bound}_{\min} / \min(\text{Cycle}(i)) \le \text{PO4Bound}_{\max} / \max(\text{Cycle}(i))$$

$$\Rightarrow \max(\text{Cycle}(i)) / \min(\text{Cycle}(i)) \le \text{PO4Bound}_{\max} / \text{PO4Bound}_{\min},$$

which is the criterion set forth earlier with max(Cycle(i))=Cycles(iMax) and min(Cycle(i))=Cycles (iMin).

To obtain this special case where:
PO4Bound$_{min(1)}$=PO4Bound$_{min(2)}$=. . . PO4Bound$_{min(n)}$=PO4Bound$_{min}$ and
PO4Bound$_{max(1)}$=PO4Bound$_{max(2)}$=. . . PO4Bound$_{max(n)}$=PO4Bound$_{max}$,
using equation (e), a is appropriately chosen. In particular, $$\text{FeedPO4conc} = a * \max(\text{FeedPO4concmin}(i)) + \quad (g)$$
$$(1-a) * \min(\text{FeedPO4concmax}(i))$$
$$= a * \max(\text{PO4Bound}_{\min(i)} / \text{Cycle}(i)) +$$
$$(1-a) * \min(\text{PO4Bound}_{\max(i)} / \text{Cycle}(i))$$
$$= a * \text{PO4Bound}_{\min} / \min(\text{Cycle}(i)) +$$
$$(1-a) * \text{PO4Bound}_{\max} / \max(\text{Cycle}(i))$$

$$\text{Choosing } a = \min(\text{Cycle}(i)) / (\max(\text{Cycle}(i) + \min(\text{Cycle}(i))), \text{ and} \quad (h)$$
$$1 - a = \max(\text{Cycle}(i)) / (\max(\text{Cycle}(i) + \min(\text{Cycle}(i))), \text{ and}$$
then substituting into equation (g), $$\text{FeedPO4conc} = \min(\text{Cycle}(i)) / (\max(\text{Cycle}(i) + \min(\text{Cycle}(i))) *$$
$$\text{PO4Bound}_{\min} / \min(\text{Cycle}(i)) + \max(\text{cycle}(i)) /$$
$$(\max(\text{Cycle}(i) + \min(\text{Cycle}(i)))) * \text{PO4Bound}_{\max} / \max(\text{Cycle}(i))$$
$$= \text{PO4Bound}_{\min} / (\max(\text{Cycle}(i) + \min(\text{Cycle}(i))) +$$
$$\text{PO4Bound}_{\max} / (\max(\text{Cycle}(i) + \min(\text{Cycle}(i)))$$
$$= (\text{PO4Bound}_{\min} + \text{PO4Bound}_{\max}) / (\max(\text{Cycle}(i) + \min(\text{Cycle}(i))),$$

which is the condition set forth earlier.

In terms of feedrate, it can be shown that the desired feedrate (FeedRate) is given by:

FeedRate = $a * \max(\text{FeedRate}_{\min(i)}) + (1 - a) * \min(\text{FeedRate}_{\max(i)})$ (e')

where $0 \leq a \leq 1$; the default value of $a$ is 0.5, and where FeedRate$_{\min(i)}$ = PO4Bound$_{\min(i)}$ / Cycle($i$) *
(TotalFeedWater) / FeedPO4, &

FeedRate$_{\max(i)}$ = PO4Bound$_{\max(i)}$ / Cycle($i$) *
(TotalFeedWater) / FeedPO4 under the condition that:

$\max(\text{PO4Bound}_{\min(i)} / \text{Cycle}(i)) \leq \min(\text{PO4Bound}_{\max(i)} / \text{Cycle}(i))$. (d')

Under this condition, any value of FeedRate in the interval defined in equation d' will maintain all the boilers in their control regions for PO4.

It should be noted that FIGS. 6 and 7 depict common normalized target regions, all of these representing a simple case of the common normalized target region of the multiple boiler MACC system 20 discussed earlier. In particular, only one dimension, namely the phosphate concentration, varies in the present ON/OFF control system 420. The common normalized target regions in FIGS. 6 and 7 are scaled by being divided by the cycles.

Back-Calculating Na

As in application Ser. No. 08/328,331, now U.S. Pat. No. 5,696,696, and as discussed earlier with respect to the MACC system 320, assuming electroneutrality in the boiler waters, a charge balance equation is used to compute effective Na concentration given PO4 and pH.

In the single boiler ON/OFF controller of application Ser. No. 08/321,338, now U.S. Pat. No. 5,696,696, it is not necessary to actually compute this Na concentration, since it is assumed that because the phosphate feed rate is proportional to blowdown flow rate, the boiler water would always be at the single, setpoint, PO4 and hence one could simply compute the pH associated with congruency ratios of 2.8:1 at that PO4 level once and for all and then use this pH setpoint as the basis for determining if the high or low Na:PO4 ratio tank were to be used.

However, at least in the general case in which all the Cycles(i) are free to "float" subject only to the above "maximum cycle ratio" constraint, it can no longer be assumed that any particular boiler will be at any particular, fixed, phosphate level; even if that boiler is not one of the boilers whose cycles change. The example at the end of the last section makes this clear: the boiler whose cycles remained fixed nonetheless moved from the lowest to the highest limit of PO4 whereas the boiler whose cycles changed did just the opposite. As with the ON/OFF controller of application Ser. No. 08/321,338, now U.S. Pat. No. 5,696,696, where an on-line PO4 meter (analyzer) 256 was not assumed to be available (hence, the broken line 460 shown between the PO4 analyzer 256 and the computer 242 in FIG. 5), it is necessary to alternatively determine the PO4 level. The PO4 level is then used to back calculate Na for the various boilers so as to determine if the pumps 234A and 234B should be turned on or off under the same constraints.

One approach would be to use the steady-state PO4(i) as given by the above equations. The problem with this approach is that, during the periods in which PO4 levels are "readjusting" to a change in cycles, the Na computed would be in error and thus the boiler water could be driven a considerable distance away from the correct congruency ratio during such periods as a result. It is therefore better to use, not the steady-state PO4 for a boiler, but rather the "model projected" PO4 in that boiler, which can be updated each time new on-line information becomes available by using the solution of the differential equation for the PO4 mass balance around the boiler (the well-known CSTR "exponential approach to equilibrium"):

PO4Est(i, t+dt)=$(1-e^{-dt/Tau(i)})$*PO4(i)+
  PO4Est(i, t)*$e^{-dt/Tau(i)}$

In the above PO4Est(i, t) is the estimated concentration of the boiler at time t (the "initial concentration") and PO4(i) is, as before, the steady-state phosphate concentration (the "final, steady-state, concentration"). Tau(i) is the boiler's characteristic time, given as Mass(i)/Blowdown(i) (where Mass(i) is the boiler water mass of the ith boiler) and dt is the time interval between samples. For cases in which the blowdown and mass of the boiler and sampling interval, dt, are fixed, this reduces to a simple EWMA (exponentially-weighted moving average) of the steady-state concentrations, with a $\lambda$ of $(1-\exp(-dt/Tau(i)))$. PO4Est(i, t) can be initialized via an initial measurement of the concentration of phosphate in each of the boilers. An alarm should be raised if this projected phosphate is outside of the phosphate control limits. In analogy with currently recommended single boiler ON/OFF control practices, this projected phosphate should be compared periodically to a manual phosphate measurement on each boiler in order to detect possible flow meter calibration errors, etc.

Note: many of the quantities, like PO4(i), Tau(i), etc., above and in what follows are also functions of time, but for simplicity this time dependence is not shown explicitly except in the case of PO4Est(i, t).

Controlling Congruency

In this ON/OFF generalization, on-line pH meters are required in every boiler, and a repetition of the PO4 projection and "pH to Na conversion" calculations described above for each boiler as well. With these numbers in hand, the Na:PO4 ratio of each boiler is computed, and the high or low Na:PO4 ratio tank is chosen based on the minimum and maximum Na:PO4 ratio among the various boilers, using NaPO4RatioBound$_{Min}$ and NaPO4RatioBound$_{Max}$ in an analogous manner to how PO4Bound$_{Min}$ and PO4Bound$_{Max}$ were used before, so that the range of congruencies of the boilers is centered within the congruency control range. Namely:

if (NaPO4Ratio($jMin$) + NaPO4Ratio($jMax$) < =

NaPO4RatioBound$_{Min}$ + NaPO4RatioBound$_{Max}$)

use high Na:PO4 ratio feed tank else use low Na:PO4 ratio feed tank

Here NaPO4Ratio(jMin), NaPO4Ratio(jMax) are the largest and smallest estimated Na:PO4 ratios.

It should be noted that the normal requirements for single boiler ON/OFF control, related to the need to limit the amount that the concentrations in a boiler can change in "deadtime hours", must be satisfied for each of the boilers in the multiple boiler configuration.

This results in control actions that move the range of congruency ratios for all boilers towards the center of the congruency range, which center is assumed to be the congruency setpoint. When cycles remain unchanged for extended periods of time, and assuming the "uniform impact of feedwater contaminants on each boiler" model is correct, it can be shown that this approach will eventually bring all of the boilers to within a "single boiler ON/OFF bounce" of the optimal congruency setpoint. (The "bounce" in the ON/OFF control system represents the largest amount that the boiler water concentration can change during the deadtime). And in many cases the controller will perform better than expected, due to the tendency of the boilers to respond in similar ways to various feed rates.

Under normal circumstances, all of the boilers should be within the congruency control range, and an alarm should be sounded if the minimum or maximum congruency ratio is beyond the corresponding Na:PO4 ratio bound. Boiler to boiler differences in the impact of contaminants on boiler water pH, phosphate hideout, etc., could result in differences from boiler to boiler that would be sufficient to sound such an alarm. If such differences are sufficiently large (e.g., lots of volatile contaminants, difference rates of breakdown, etc.) it could make controlling congruency within the limitations imposed by a common feedpoint in a common feedwater impossible. However, for totally ionized, and therefore non-volatile, contaminants, this should not be an issue.

At first blush, an alternative approach would be to only measure pH on one of the boilers and use that pH to estimate the sodium leak in the feedwater line, and then use this leak along with known sodium feedrates, to project the sodium, and hence the sodium phosphate ratio, in all the boilers, without the need to actually have a pH meter on each boiler. However, a potential problem with doing that is that it depends too heavily on the idea that all feedwater contaminants, once they reach the boiler water, have the same impact on boiler water effective sodium regardless of boiler conditions. For example, if a certain contaminant is a volatile chemical, its contribution to the "effective sodium leak" that would show up in the pH of a boiler would vary depending upon the volatility of the chemical (which, in turn, would depend on such things as the temperature and pH of the boiler water). This "uniform boiler water impact" is a much more dubious assumption upon which to estimate "effective sodium" in the boiler water than the assumptions behind our phosphate estimation method. Moreover, these phosphate estimation assumptions have at least partially been validated by the current ON/OFF controller, something the "uniform boiler water impact assumption" cannot claim.

Furthermore, it would appear that one could safely rely upon the similarity of the response of all of the boilers as they move between the corresponding high and low Na:PO4 ratio lines, to base the congruency control action on just one, lead boiler. At first glance, it may appear desirable to use a simple-lead-boiler type of congruency control, in conjunction with the ratioed approach to controlling overall feed rate given above. But there are a number of potential problems to this approach, including:

The rate at which concentrations of each boiler change in response to switching between the two feed tanks will differ, and if only the lead boiler's congruency ratio is monitored, the difference in the size of the "ON/OFF bounce" that this difference in responsiveness causes could create problems with keeping all boilers in the box.

It can be shown that if cycle changes are large, this approach can lead to large excursions out of the box during that period when the steady-state phosphate concentrations have not yet re-adjusted to the new levels associated with the new cycles, because the "high" and "low" feed tank steady-state concentrations toward which the boiler waters are moving have already assumed their new, and sometimes dramatically different in impact on congruency, positions. In such conditions, the congruency response of each boiler can be very different until the new steady-state PO4 concentrations are reached. The result is that during load swings, such a lead boiler controller could appear to "be out of control" (e.g., driving certain boilers way out of the box) until the new steady-state phosphate concentrations were reached.

Moreover, the same objections regarding the over-dependence on the uniform impact of feedwater contaminants made above would apply to this lead boiler approach as well. In general, a "lead boiler" though it is often a good "role model" for the other boiler's to follow, is probably just different enough to make this idea unworkable. With certain, less demandingly-variable systems, a lead boiler approach is possible, but in the general case, the boiler's performance would tend to be bumped way out of its congruency range during a rapid load swing, etc. Such boiler behavior would be undesirable to customer satisfaction.

Therefore, the more conservative strategy of actually measuring pH and computing congruency in every boiler (using only the model projected phosphate), and basing the congruency portion of the controller directly on these congruency ratios, appears more reliable. In addition, this method permits display of on-line pH, cycles, estimated phosphate and estimated congruency ratio for each boiler, all of which are desirable information for customer use. This approach also avoids having to actually select one boiler over another which may not always be an easy choice to make.

Summary of the Multi-Boiler ON/OFF Control Method:

1) Use the same configuration of pumps and feed tank concentrations currently in use for single boiler ON/OFF defined in application Ser. No. 08/321,338, now U.S. Pat. No. 5,696,696, with the pumping into the common feedwater header performed in such a manner that concentrations are well-mixed before the header splits into the various individual boiler feed lines. Also, the dead-time requirements for single boiler ON/OFF (related to the length of pH samples lines, frequency of sampling, etc.) need to be satisfied for each boiler in the multiple boiler system individually.

2) Each boiler needs an on-line pH, and on-line blowdown flow, and an on-line steam flow measurement (These flow rates can be summed to provide the on-line total feedwater flow required by the algorithm).

3) The total feed rate from the currently selected feed tank is given by the formula:

$$\text{FeedRate}=a*\max(\text{FeedRate}_{min(i)})+(1-a)*\min(\text{FeedRate}_{max(i)})$$

where $0<a<1$; the default value of a is 0.5, and where $\text{FeedRate}_{min(i)}=\text{PO4Bound}_{min(i)}/\text{Cycle}(i)*(\text{TotalFeedWater})/\text{FeedPO4}$, & $\text{FeedRate}_{max(i)}=\text{PO4Bound}_{max(i)}/\text{Cycle}(i)*(\text{TotalFeedWater})/\text{FeedPO4}$ Warnings are sounded if the following constraint is violated:

$$\max(\text{PO4Bound}_{min(i)}/\text{Cycle}(i))<\min(\text{PO4Bound}_{max(i)}/\text{Cycle}(i)).$$

Or, where $\text{PO4Bound}_{min(1)}=\text{PO4Bound}_{min(2)}=\ldots \text{PO4Bound}_{min(n)}=\text{PO4Bound}_{min}$ and $\text{PO4Bound}_{max(1)}=\text{PO4Bound}_{max(2)}=\ldots \text{PO4Bound}_{max(n)}=\text{PO4Bound}_{max}$, $$\text{FeedRate}=(\text{TotalFeedWater}/\text{FeedPO4}) * (\text{PO4Bound}_{Max}+\text{PO4Bound}_{Min})/(\text{Cycles}(i\text{Max})+\text{Cycles}(i\text{Min}))$$

Warnings are sounded if the following maximum cycle ratio constraint is violated:

$$\text{Cycles}(i\text{Max})/\text{Cycles}(i\text{Min})<=\text{PO4Bound}_{Max}/\text{PO4Bound}_{Min}$$

4) The steady-state phosphate of each boiler is calculated, and estimates for the current PO4 concentration of each boiler updated:

Steady-state concentration:

$$PO4(i) = FeedRate * FeedPO4 * Cycles(i)/TotalFeedWater$$

(Note: despite the name, this steady-state concentration will in general vary each time new measurements become available).

Current phosphate estimate in each boiler updated via the "EWMA-like" formula:

$$PO4Est(i, t+dt) = (1 - e^{-dt/Tau(i)}) * PO4(i) + PO4Est(i, t) * e^{-dt/Tau(i)}$$

The above equation is initialized by a manual sample from each boiler, from which the initial phosphate concentration is measured. (Periodic manual samples to check blowdown flow meter calibration, etc., as currently practiced with single boiler ON/OFF, should be done on each boiler as well). Alarms are sounded if any of these projected phosphates are outside of the phosphate control limits. Note that Tau(i)=M(i)/B(i) is a function of blowdown, and will therefore change over time.

5) The measured pH and estimated phosphate of each boiler is used in a charge balance equation, assuming electroneutrality in the boiler waters, to estimate the effective Na concentration and to determine the Na:PO4 ratio of each boiler:

$$NaPO4Ratio(i) = Na_{effective}(i / PO4Est(i, t)$$

6) The high or low Na:PO4 ratio feed tank is selected based on if the middle of the range spanned by all the estimated Na:PO4 ratios is above or below the middle of the range of allowed congruency ratios:

if (NaPO4Ratio(jMin) + NaPO4Ratio(jMax) < =

NaPO4RatioBound$_{Min}$ + NaPO4RatioBound$_{Max}$)

use high Na:PO4 ratio tank else use low Na:PO4 ratio tank

Alarms are sounded if these minimum or maximum congruency ratios are not within their corresponding bounds.

Without further elaboration, the foregoing will so fully illustrate our invention that others may, by applying current or future knowledge, readily adopt the same for use under various conditions of service.

We claim:

1. A method for controlling at least two interdependent chemicals in the fluids of at least two continuously stirred tank reactors (CSTRs) having respective blowdown flows and steam rate flows defining respective cycles for each of said CSTRs, said at least two interdependent chemicals being fed to said fluids through a common feedwater to each of said at least two CSTRs, said method comprising the steps of:
   (a) establishing a respective mathematical model of each of said CSTRs;
   (b) monitoring the concentration of one of said at least two interdependent chemicals in each of the fluids, the temperature at which the pH is measured in each of the fluids, the respective blowdown flow and the respective steam rate flow;
   (c) updating the models based on the concentration of said one of said at least two interdependent chemicals in each of the fluids, the pH of each of the fluids, the temperature at which the pH is measured in each of the fluids, the respective blowdown flow and the respective steam rate flow;
   (d) defining a respective target region of said at least two interdependent chemicals in said respective continuously stirred tank reactors and wherein said respective target regions are scaled according to the respective cycles, said respective target regions establishing a state of congruency for each of the fluids;
   (e) providing a feedstream of a high-pH fluid treatment material comprising a mixture of said at least two interdependent chemicals and a feedstream of a low-pH fluid treatment material comprising a mixture of said at least two interdependent chemicals for feeding, at respective feed rates, to the fluids; and
   (f) developing an optimum feed rate program for controlling said feedstreams to automatically minimize the time that said at least two interdependent chemicals in the fluids spend outside of a common normalized target region formed by the intersection of said respective target regions.

2. The method of claim 1 wherein each of said fluids has associated therewith a respective pumpable region in a CSTR state space that defines all reachable concentrations of said at least two interdependent chemicals in the respective fluid and including therein said respective target region for defining congruency of said at least two interdependent chemicals in said respective pumpable region, said respective pumpable region also being scaled according to said respective cycles, said step of developing an optimum feed rate program comprising overlaying said respective pumpable regions and said respective target regions to define a single pumpable region and to establish said common normalized target region defined by the intersection of said overlayed respective target regions.

3. The method of claim 2 wherein said fluids comprise respective current concentrations of said at least two interdependent chemicals and wherein said step of developing an optimum feed rate program comprises the steps of:
   (a) establishing a respective region formed by the endpoints of all feed trajectories that move said respective current concentrations of said fluids into said common normalized target region;
   (b) selecting a new region formed by the intersection of said respective regions, said new region formed by the intersection of said respective regions defining a common normalized pumpable region.

4. The method of claim 3 wherein said common normalized target region comprises vertices, including extreme vertices, and edges and wherein said step of establishing a respective region comprises forming a respective region defined by feed trajectories that originate from said current concentrations and intersect said extreme vertices for each of said respective current concentrations of said fluids.

5. The method of claim 4 wherein said step of developing an optimum feed rate program further comprises the step of evaluating, for each of said continuously stirred tank reactors, sets of feed rate trajectories between the current concentrations of said at least two interdependent chemicals and said common normalized target region to determine the time required to move said current concentrations into said common normalized target region.

6. The method of claim 5 wherein said common normalized pumpable region comprises vertices and edges, together which define a common normalized pumpable region perimeter, and wherein said step of evaluating comprises the steps of:

(a) determining the time associated with driving the current concentrations of said at least two interdependent chemicals in each of said fluids along a first set of feed rate trajectories formed between the current concentrations and said vertices of said common normalized pumpable region;

(b) determining the time associated with driving the current concentrations of said at least two interdependent chemicals in each of said fluids along a second set of feed rate trajectories formed between said current concentrations and said common normalized target region vertices, said second set of feed rates being projected until they intersect said common normalized pumpable region perimeter, if at all, to define a third set of feed rate trajectories; and (c) selecting one feed rate trajectory, from all of said first and third sets of feed rate trajectories from each of said fluids, that requires the least amount of time for at least one fluid to reach an edge of said common normalized target region.

7. The method of claim 6 wherein said feedstream of a high-pH fluid treatment material comprising a mixture of said at least two interdependent chemicals defines a first feedstream and wherein said feedstream of a low-pH fluid treatment material comprising a mixture of said at least two interdependent chemicals defines a second feedstream and wherein said selected one feed rate trajectory comprises an endpoint and wherein said method further comprises the step of determining how long to feed said first and second feedstreams at said selected one feed rate trajectory, said step of determining how long to feed said first and second feedstreams comprising the steps of:

(a) for each of said at least two CSTR fluids, establishing a respective feed rate trajectory defined by a line from said respective current concentrations of said at least two interdependent chemicals to the endpoint of said selected one feed rate trajectory;

(b) for each of said at least two CSTR fluids, determining the point at which said respective feed rate trajectory intersects an edge of said common normalized target region and determining the time associated with moving said current concentrations to said point, said intersected edge being a common normalized target region edge different from said edge reached by said at least one fluid in the least amount of time; and (c) selecting the minimum of those times associated with moving said current concentrations to said point.

8. The method of claim 7 further comprising the step of feeding said first and second feedstreams at said selected one feed rate trajectory for an amount of time corresponding to said selected minimum of those times associated with moving said current concentrations to said point.

9. The method of claim 8 wherein each of said CSTR state spaces are updated based on said feeding said first and second feedstreams at said selected one feed rate trajectory for said selected minimum of those times associated with moving said current concentrations to said point.

10. The method of claim 9 further comprising the steps of:

(a) establishing a new common normalized target region that is nested within said common normalized target region; and (b) repeating the steps of selecting one feed rate trajectory that requires the least amount of time for at least one fluid to reach an edge of said new common normalized target region; and (c) repeating the steps for determining how long to feed said first and second feedstreams.

11. The method of claim 7 further comprising the step of feeding said first and second feedstream at said selected one feed rate trajectory for an amount of time corresponding to the time it takes for new data to be available, said data being defined as said concentration of said one of said at least two interdependent chemicals in the fluids, said pH of said fluids, said temperature at which the pH is measured, said blowdown flow and said steam rate flow.

12. The method of claim 11 wherein each of said fluid state spaces are updated based on said feeding said first and second feedstreams at said selected one feed rate trajectory for said amount of time corresponding to the time it takes for new data to be available.

13. The method of claim 11 wherein a new common normalized target region is recomputed based on said new data.

14. The method of claim 2 wherein said feedstream of a high-pH fluid treatment material comprising a mixture of said at least two interdependent chemicals defines a first feedstream and wherein said feedstream of a low-pH fluid treatment material comprising a mixture of said at least two interdependent chemicals defines a second feedstream and wherein said fluids comprise respective current concentrations of said at least two interdependent chemicals and wherein said step of developing an optimum feed rate program comprises the steps of:

(a) evaluating, for each of said CSTRs, sets of feed rate trajectories between the current concentrations of said at least two interdependent chemicals and said common normalized target region to determine the time required to move said current concentrations into said common normalized target region;

(b) selecting that feed rate trajectory that moves at least one fluid current concentrations into said common normalized target region in the least amount of time; and (c) feeding said first and second feedstreams at said selected feed rate trajectory.

15. The method of claim 14 further comprising the steps of:

(a) establishing a new common normalized target region that is nested within said common normalized target region; and (b) evaluating, for each of said CSTRs, sets of feed rate trajectories between the current concentrations of said at least two interdependent chemicals and said new common normalized target region to determine the time required to move said current concentrations into said new common normalized target region:

(b) selecting a feed rate trajectory that moves at least one fluid current concentrations into said new common normalized target region in the least amount of time; and (c) feeding said first and second feedstreams at said selected feed rate trajectory.

16. The method of claim 1 wherein each of said CSTRs is an industrial boiler having a boiler fluid.

17. The method of claim 16 wherein said one of said at least two interdependent chemicals is phosphate.

18. The method of claim 17 wherein said one of said at least two interdependent chemicals is sodium.

19. The method of claim 18 wherein said method further includes the step of estimating the blowdown flow.

20. The method of claim 19 wherein said method further includes the steps of calculating the phosphate concentration and the sodium concentration in the boiler fluid.

21. The method of claim 20 wherein said method further includes the step of estimating a feedwater contaminant ingress.

22. The method of claim 21 wherein said steps of estimating a blowdown flow and a feedwater contaminant ingress are based on a series of phosphate and pH measurements of the boiler fluid wherein said method uses small sample intervals.

23. The method of claim 1 wherein said method further includes a step that accounts for dead time in each of the continuously stirred tank reactors.

24. The method of claim 1 wherein said method further comprises the step of controlling the blowdown flow of each of said CSTRs.

25. An automatic control system for controlling at least two interdependent chemicals in the fluids of at least two continuously stirred tank reactors (CSTRs) linked in parallel by a common feedwater line and wherein each CSTR includes a respective blowdown flow and steam rate flow that define respective cycles for each of said CSTRs and wherein each CSTR has associated therewith a respective target region of said at least two interdependent chemicals, said respective target regions being scaled according to the respective cycles of said CSTRs, said control system comprising:

input means for receipt of fluid parameters and control means responsive to said input means;

said control means using non-proportional control for automatically minimizing the time that said at least two interdependent chemicals in the fluids spend outside of a common normalized target region formed by the intersection of said respective target regions of said at least two CSTRs;

wherein one of said fluid parameters comprises the pH of the fluid and wherein said input means comprises means for determining the pH value of each of the fluids; and wherein said control means comprises a first feedstream and a second feedstream for feeding first and second fluid treatment materials, respectively, to the common feedwater line at respectively determined feed rates, said first material comprising a mixture of sodium and phosphate having a first predetermined sodium-to-phosphate ratio and said second material comprising a mixture of sodium and phosphate having a second predetermined sodium-to-phosphate ratio.

26. The control system of claim 25 wherein said control means further comprises an adaptive controller, said adaptive controller modeling of each of said at least two CSTRs.

27. The control system of claim 26 wherein said control means further comprises monitoring means for monitoring the concentration of said at least two interdependent chemicals in said fluids, the temperature at which the pH is measured, the blowdown flow and the steam rate flow, said monitoring means being coupled to said adaptive controller in order to update said modeling of each of said at least two CSTRs, the concentration of said at least two interdependent chemicals in said fluids, the temperature at which the pH is measured, the blowdown flow and the steam rate flow being defined as data.

28. The control system of claim 27 wherein said adaptive controller generates said respective target regions [of congruency] in a CSTR state space for each of said at least two CSTRs.

29. The control system of claim 28 wherein said adaptive controller overlays said respective target regions to generate said common normalized target region.

30. The control system of claim 29 wherein each fluid comprises a current concentration for each of said at least two interdependent chemicals and wherein said adaptive controller analyzes all feed rate trajectories of said first and second feedstreams that will drive said current concentrations in each of said fluids from said current concentrations to concentrations within said common normalized target region in said CSTR state space, said analyzation determining a respective region for each of said fluids that is formed by the endpoints of all said feed rate trajectories.

31. The control system of claim 30 wherein said adaptive controller selects that region in said CSTR state space that is formed by the intersection of said respective regions, said selected region forming a common normalized pumpable region that defines all reachable concentrations of said at least two interdependent chemicals among said at least two CSTR fluids, said common normalized pumpable region comprising a first set of edges and a first set of vertices.

32. The control system of claim 31 wherein said common normalized target region comprises a second set of vertices and second set of edges, said adaptive controller determining for each of said CSTRs:

(a) the time associated with driving said current concentrations of said at least two interdependent chemicals along a first set of feed rate trajectories formed between said current concentrations and said second set of vertices; and (b) the time associated with driving said current concentrations of said at least two interdependent chemicals along a second set of feed rate trajectories formed between said current concentrations and said second set of vertices, said second set of feed rate trajectories being projected until they intersect said first set of edges of said common normalized pumpable region to define a third set of feed rate trajectories, said adaptive controller selecting one feed rate trajectory from all of said first and third sets of feed rate trajectories that requires the least amount of time for at least one fluid to reach one of said second set of edges.

33. The control system of claim 32 wherein said adaptive controller calculates how long to feed said first and second feedstreams at said selected feedrate trajectory, said adaptive controller:

(a) establishing, for the other CSTRs of said at least two CSTRs whose current concentrations have not reached one of said second set of edges, a respective feedrate trajectory between said current concentrations and said selected feedrate trajectory;

(b) said adaptive controller determining, for the other CSTRs whose current concentrations have not reached one of said second set of edges, the point at which each of said respective feedrate trajectories intersects one of said second set of edges and determining the time associated with moving said current concentrations to said point, said intersected edge being a common normalized target region edge different from said edge of said common normalized target region reached by said at least one CSTR fluid in the least amount of time, said adaptive controller selecting the minimum of those times associated with moving said current concentrations to said point and feeding said first and second feedstreams at said selected feedrates for said selected minimum time.

34. The control system of claim 33 wherein said monitoring means updates said fluid state spaces for each of said CSTRs based on said adaptive controller feeding said first and second feedstreams at said selected feedrate trajectories for said selected minimum time.

35. The control system of claim 34 wherein said adaptive controller establishes a new common normalized target region that is nested within said common normalized target region and wherein said adaptive controller determines one feedrate trajectory that requires the least amount of time for at least one of said CSTRs to reach an edge of said new common normalized target region and determines how long to feed said first and second feedstreams at said one feedrate trajectory.

36. The control system of claim 32 wherein said adaptive controller feeds said first and second feedstreams at said selected feedrates for an amount of time corresponding to the time it takes for new data to be available.

37. The control system of claim 36 wherein said monitoring means updates said CSTR state spaces for each of said CSTRs based on said adaptive controller feeding said first and second feedstreams at said selected feedrate trajectories for said time it takes for new data to be available.

38. The control system of claim 37 wherein said adaptive controller recomputes a new common normalized target region based on said new data.

39. A method for controlling the sodium-to-phosphate ratio of the fluids of at least two continuously stirred tank reactors (CSTRs) having respective blowdown flows and steam rate flows defining respective cycles for each of said at least two continuously stirred tank reactor, said fluids of said at least two CSTRs being fed a through a common feedwater line, said method comprising the steps of:
(a) providing a supply of a first sodium phosphate fluid treatment material to said common feedwater, said first sodium phosphate fluid treatment material having a first predetermined sodium-to-phosphate ratio and a first known phosphate concentration;
(b) providing a supply of a second sodium phosphate fluid treatment material to said common feedwater, said second sodium phosphate fluid treatment material having a second predetermined sodium-to-phosphate ratio and a second known phosphate concentration;
(c) measuring a fluid parameter of each of said fluids substantially continuously;
(d) determining the cycle of each of said at least two CSTRs substantially continuously;
(e) estimating the phosphate concentration in each of said fluids;
(f) determining the effective sodium in each of said fluids;
(g) determining the sodium-to-phosphate ratio in each of said fluids and identifying a maximum sodium-to-phosphate ratio and a minimum sodium-to-phosphate ratio among said fluids, said minimum and maximum sodium-to-phosphate ratios defining a first range having a first midpoint; and
(h) feeding said first sodium phosphate fluid treatment material if said first midpoint is less than or equal to a second midpoint of a predetermined ratio range of sodium-to-phosphate, or feeding said second sodium phosphate fluid treatment material if said first midpoint is greater than said second midpoint.

40. The method of claim 39 wherein said step of determining the cycle of each of said at least two CSTRs substantially continuously comprises the steps of:
(a) measuring each of said blowdown flows substantially continuously; and
(b) measuring the total feedwater flow substantially continuously.

41. The method of claim 40 wherein said step of feeding said first sodium phosphate fluid treatment material or said second sodium phosphate fluid treatment material comprises feeding said first or second sodium phosphate fluid treatment material at a rate which maintains the respective phosphate concentration of each boiler fluid between a respective predetermined upper phosphate control limit and a respective predetermined lower phosphate control limit.

42. The method of claim 41 wherein said respective predetermined upper phosphate control limits are identical and which form a first phosphate control limit, and wherein said respective predetermined lower phosphate control limits are identical and which form a second phosphate control limit.

43. The method of claim 42 wherein said step of feeding said first sodium phosphate fluid treatment material or said second sodium phosphate fluid treatment material is fed at a rate given by:

$$Feedrate = \left(\frac{TotalFeedWater}{FeedPO4}\right)\frac{(PO4Bound_{max} + PO4Bound_{min})}{(Cycles_{imax} + Cycles_{imin})}$$

where TotalFeedwater is said total feedwater flow;
FeedPO4 is said first known phosphate concentration or said second known phosphate concentration, depending on which fluid treatment material is being fed;
$PO4Bound_{max}$ is said first phosphate control limit;
$PO4Bound_{min}$ is said second phosphate control limit;
$Cycles_{imax}$ is said CSTR having a maximum cycle value wherein said cycle is defined as:

$$Cycle(i) = \frac{(Steam(i) + Blowdown(i))}{Blowdown(i)}$$

and $Cycles_{imin}$ is said CSTR having a minimum cycle value, Steam (i) is the steam flow rate for the "ith" boiler and Blowdown (i) is the blowdown flow for the "ith" CSTR and i=CSTR index for identifying a particular CSTR of said at least two CSTRs.

44. The method of claim 43 wherein said step of feeding said first sodium phosphate fluid treatment material or said second sodium phosphate fluid treatment material at said rate occurs as long as the following condition is met:

$Cycles_{imax}/Cycles_{imin} \leq PO4Bound_{max}/PO4Bound_{min}$.

45. The method of claim 41 wherein said step of feeding said first sodium phosphate fluid treatment material or said second sodium phosphate fluid treatment material is fed at a rate given by:

$$FeedRate = a * max(FeedRate_{min(i)}) + (1 - a) * min(FeedRate_{max(i)}),$$

where $0 \leq a \leq 1$;

$i =$ CSTR index for identifying a particular CSTR of said at least two CSTRs;

$FeedRate_{min(i)} = PO4Bound_{min(i)} / Cycle(i) * (TotalFeedWater) / FeedPO4;$ $FeedRate_{max(i)} = PO4Bound_{max(i)} / Cycle(i) * (TotalFeedWater) / FeedPO4$ -continued TotalFeedwater is said total feedwater flow;

FeedPO4 is said first known phosphate concentration or said second known phosphate concentration, depending on which fluid treatment material is being fed;

PO4Bound$_{max(i)}$ is said respective predetermined upper phosphate control limit;

PO4Bound$_{min(i)}$ is said respective predetermined lower phosphate control limit; and Cycle($i$) is defined as:

$$\text{Cycle}(i) = \frac{(\text{Steam}(i) + \text{Blowdown}(i))}{\text{Blowdown}(i)}.$$

46. The method of claim 45 wherein said step of feeding said first sodium phosphate fluid treatment material or said second sodium phosphate fluid treatment at said rate occurs as long as the following condition is met:

max(PO4Bound$_{min(i)}$/Cycle(i)) ≦ min(PO4Bound$_{max(i)}$/Cycle(i)).

47. The method of claim 46 wherein said step of determining the effective sodium in each of said fluids comprises back calculating sodium using a model projected phosphate concentration given by:

$$\text{PO4Est}(i, t+dt) = \left(1 - e^{-\frac{dt}{\tau(i)}}\right)\text{PO4}(i) + \text{PO4Est}(i, t)e^{-\frac{dt}{\tau(i)}}$$

where

PO4Est(i,t) is the estimated concentration in the fluid at time t;

i=CSTR index for identifying a particular CSTR of said at least two CSTRs;

PO4(i) is the steady-state phosphate concentration;

T is the characteristic time of the fluid; and dt is the time between interval samples.

48. The method of claim 41 wherein said fluid parameter is the pH of the fluid.

49. The method of claim 41 wherein said first known phosphate concentration is identical to said second known phosphate concentration.

50. The method of claim 39 wherein said method further comprises the step of controlling the blowdown flow of each of said CSTRs.

51. A system for simultaneously controlling respective sodium-to-phosphate ratios of at least two boiler fluids of respective industrial boilers that are fed through a common feedwater, the industrial boilers having respective blowdown flows and steam rate flows that define respective cycles for each boiler fluid, said system comprising:

input means for receipt of a boiler fluid parameter for each of the at least two boiler fluids and a parameter indicative of the cycles of each of said industrial boilers; and control means responsive to said input means for automatically driving the respective sodium-to-phosphate ratios of said at least two boiler fluids to a desired sodium-to-phosphate ratio region, said control means comprising model phosphate projecting means for estimating the sodium-to-phosphate ratios in each of said at least two boiler fluids.

52. The system of claim 51 wherein said boiler fluid parameter comprises the pH of the boiler fluid, the respective pH of each of the boiler fluids being defined by the respective sodium-to-phosphate ratio and the respective cycles and wherein said input means comprises a respective pH meter for determining the respective pH value of each of the boiler fluids and providing the respective pH value to said control means.

53. The system of claim 51 wherein said control means comprises a first feedstream and a second feedstream for feeding first and second fluid treatment materials, respectively, to the common feedwater, said first material comprising a mixture of sodium and phosphate having a first predetermined sodium-to-phosphate ratio and a first predetermined concentration of phosphate, said second material comprising a mixture of sodium and phosphate having a second predetermined sodium-to-phosphate ratio and a second predetermined concentration of phosphate.

54. The system of claim 53 wherein said first predetermined concentration of phosphate and said second predetermined concentration of phosphate are identical.

55. The system of claim 53 wherein said control means comprises feeding means for feeding said first feedstream or said second feedstream at a rate which maintains the respective phosphate concentration of each boiler fluid between a respective predetermined upper phosphate control limit and a respective predetermined lower phosphate control limit.

56. The system of claim 55 wherein said respective predetermined upper phosphate control limits are identical, referred to as a first phosphate control limit, and wherein said respective predetermined lower phosphate control limits are identical, referred to as a second phosphate control limit.

57. The system of claim 56 wherein said control means further comprises means for feeding said first feedstream or said second feedstream at a rate given by:

$$\text{Feedrate} = \left(\frac{\text{TotalFeedWater}}{\text{FeedPO4}}\right)\frac{(\text{PO4Bound}_{max} + \text{PO4Bound}_{min})}{(\text{Cycles}_{imax} + \text{Cycles}_{imin})}$$

where

TotalFeedwater is the flow of said common feedwater;

FeedPO4 is said first predetermined phosphate concentration or said second predetermined phosphate concentration;

PO4Bound$_{max}$ is a predetermined maximum phosphate concentration;

PO4Bound$_{min}$ is a predetermined minimum phosphate concentration;

Cycles$_{imax}$ is said boiler having a maximum cycle value wherein said cycle is defined as:

$$\text{Cycle} = \frac{(\text{Steam}(i) + \text{Blowdown}(i))}{\text{Blowdown}(i)}$$

and Cycles$_{imin}$ is said boiler having a minimum cycle value, Steam (i) is the steam flow rate for the "ith" boiler and Blowdown (i) is the blowdown flow for the "ith" boiler and i=boiler index for identifying a particular boiler of said at least two boilers.

58. The system of claim 57 wherein said feeding means includes monitoring means that permits said feeding means to feed at said rate whenever the following condition is met:

Cycles$_{imax}$/Cycles$_{imin}$ ≦ PO4Bound$_{max}$/PO4Bound$_{min}$.

59. The system of claim 58 wherein said monitoring means alerts an operator if said condition is not met.

60. The system of claim 55 wherein said feeding means feeds said first feedstream or said second feedstream at a rate given by:

FeedRate=a*max(FeedRate$_{min(i)}$)+(1-a)*min(FeedRate$_{max(i)}$), where

0≦a≦1;

i=boiler index for identifying a particular boiler of said at least two boilers;

FeedRate$_{min(i)}$=PO4Bound$_{min}$/Cycle(i)*(TotalFeedWater)/FeedPO4;

FeedRate$_{max(i)}$=PO4Bound$_{max(i)}$/Cycle(i)*(TotalFeedWater)/FeedPO4

TotalFeedwater is the flow of said common feedwater;

FeedPO4 is said first predetermined phosphate concentration or said second predetermined phosphate concentration, depending on which fluid treatment material is being fed;

PO4Bound$_{max(i)}$ is said respective predetermined upper phosphate control limit;

PO4Bound$_{min(i)}$ is said respective predetermined lower phosphate control limit; and Cycle(i) is defined as:

$$Cycle(i) = \frac{(Steam(i) + Blowdown(i))}{Blowdown(i)}.$$

61. The system of claim 60 wherein said feeding means includes monitoring means that permits said feeding means to feed at said rate whenever the following condition is met:

max(PO4Bound$_{min(i)}$/Cycle(i))≦min(PO4Bound$_{max(i)}$/Cycle(i)).

62. The system of claim 61 wherein said control means further comprises means for estimating the phosphate concentration in each of the boiler fluids.

63. The system of claim 62 wherein said control means further comprises means for back-calculating the sodium concentration in each of said boiler fluids.

64. The system of claim 63 wherein said means for back-calculating the sodium concentration in each of said boiler fluids uses the following model projected phosphate concentration:

$$PO4Est(i, t+dt) = \left(1 - e^{-\frac{dt}{\tau(i)}}\right)PO4(i) + PO4Est(i, t)e^{-\frac{dt}{\tau(i)}}$$

where

PO4Est(i,t) is the estimated concentration in the fluid at time t;

i=boiler index for identifying a particular boiler of said at least two boilers;

PO4(i) is the steady-state phosphate concentration;

T is the characteristic time of the fluid; and dt is the time between interval samples.

65. The system of claim 62 wherein said control means further comprises means for determining a sodium-to-phosphate ratio for each of said boiler fluids and for identifying a maximum sodium-to-phosphate ratio and a minimum sodium-to-phosphate ratio from all of said boiler fluids to define a first range having a first midpoint.

66. The system of claim 62 wherein said feeding means feeds said first feedstream if said first midpoint is less than or equal to a second midpoint of a predetermined ratio range of sodium-to-phosphate, or feeding said second feedstream if said first midpoint is greater than said second midpoint.

67. The system of claim 61 wherein said monitoring means alerts an operator if said condition is not met.

68. The system of claim 51 wherein said system does not control the blowdown flow of each of said boilers.

* * * * *